(12) United States Patent
Olympio

(10) Patent No.: US 10,245,055 B2
(45) Date of Patent: Apr. 2, 2019

(54) DEVICES THAT ALLOW FOR RAPID CHANGE OUT OF ENDOTRACHEAL (ET) TUBES AND RELATED METHODS

(71) Applicant: Michael A. Olympio, Winston-Salem, NC (US)

(72) Inventor: Michael A. Olympio, Winston-Salem, NC (US)

(73) Assignee: Michael A. Olympio, Winston-Salem, NC (US)

( * ) Notice: Subject to any disclaimer, the term of this patent is extended or adjusted under 35 U.S.C. 154(b) by 960 days.

(21) Appl. No.: 14/740,783

(22) Filed: Jun. 16, 2015

(65) Prior Publication Data
US 2015/0283344 A1    Oct. 8, 2015

Related U.S. Application Data

(63) Continuation-in-part of application No. 14/104,481, filed on Dec. 12, 2013, now Pat. No. 9,669,175.

(60) Provisional application No. 61/738,583, filed on Dec. 18, 2012, provisional application No. 61/766,790, filed on Feb. 20, 2013.

(51) Int. Cl.
   *A61B 17/28*     (2006.01)
   *A61B 17/32*     (2006.01)
   *A61M 16/04*    (2006.01)

(52) U.S. Cl.
   CPC .............. *A61B 17/28* (2013.01); *A61B 17/32* (2013.01); *A61M 16/0493* (2014.02)

(58) Field of Classification Search
   CPC ...... A61M 16/0488–16/0497; A61M 25/0097; A61M 25/0169; A61M 2025/0183; A61M 2025/022; A61M 2025/0675; A61B 17/28; A61B 17/32
   See application file for complete search history.

(56) References Cited

U.S. PATENT DOCUMENTS

| | | | |
|---|---|---|---|
| 4,270,529 A | 6/1981 | Muto | |
| 4,473,067 A | 9/1984 | Schiff | |
| 4,687,470 A | 8/1987 | Okada | |
| 4,848,331 A | 7/1989 | Northway-Meyer | |
| 4,960,122 A | 10/1990 | Mizus | |
| 4,997,424 A * | 3/1991 | Little | A61M 25/0668 30/90.4 |

(Continued)

FOREIGN PATENT DOCUMENTS

| WO | WO 97/18002 A1 | 5/1997 |
|---|---|---|
| WO | WO 2014/099780 A1 | 6/2014 |

OTHER PUBLICATIONS

Endotracheal Tube Holder, Product Example, GMEDI Co. Ltd., http://www.gobizkorea.com/catalog/product_list, date unknown but believed to be before the priority date of the present application, printed from the internet Nov. 19, 2012, 2 pages.
Hudes et al., Difficult Endotracheal Reintubations: A Simple Technique, Anesthesiology, 1986, pp. 515-517, vol. 64.
International Search Report and Written Opinion for related PCT Application No. PCT/US2013/075386, dated Apr. 3, 2014.

(Continued)

*Primary Examiner* — Valerie L Woodward
(74) *Attorney, Agent, or Firm* — Myers Bigel, P.A.

(57) ABSTRACT

Devices for tracheal tubes include: (a) a mouthpiece sized and configured to allow an endotracheal tube to extend outwardly therefrom; and (b) a handle including a cutting member that can attach to the mouthpiece. The mouthpiece can include at least one outwardly projecting substantially rigid short tube defining an open channel. The handle can releasably attach to the short tube.

8 Claims, 25 Drawing Sheets

(56) References Cited

U.S. PATENT DOCUMENTS

| | | | |
|---|---|---|---|
| 5,052,386 A | | 10/1991 | Fischer |
| 5,188,606 A | | 2/1993 | Maloney et al. |
| 5,211,655 A | | 5/1993 | Hasson |
| 5,261,887 A | * | 11/1993 | Walker .............. A61M 25/0668 604/161 |
| 5,330,460 A | | 7/1994 | Moss et al. |
| 5,636,625 A | | 6/1997 | Miyagi et al. |
| 5,829,430 A | | 11/1998 | Islava |
| 5,873,858 A | | 2/1999 | Schafer et al. |
| 6,159,198 A | * | 12/2000 | Gardeski ........... A61M 25/0668 604/161 |
| 6,497,681 B1 | * | 12/2002 | Brenner ............ A61M 25/0668 604/160 |
| 7,950,155 B2 | * | 5/2011 | Goode .................. A61F 2/4611 30/280 |
| 7,963,040 B2 | * | 6/2011 | Shan .................... A61M 25/06 30/90.1 |
| 2006/0272647 A1 | | 12/2006 | Hauge |
| 2008/0092901 A1 | | 4/2008 | Kang |
| 2009/0049698 A1 | | 2/2009 | Drake et al. |
| 2009/0084377 A1 | | 4/2009 | Hajgato |
| 2009/0253964 A1 | | 10/2009 | Miyamoto |
| 2009/0255538 A1 | | 10/2009 | Thomson et al. |
| 2010/0030161 A1 | * | 2/2010 | Duffy ................ A61M 25/0668 604/246 |
| 2010/0213241 A1 | | 8/2010 | Bedi |
| 2011/0023871 A1 | * | 2/2011 | Pacey ................... A61M 16/04 128/200.26 |
| 2014/0166000 A1 | | 6/2014 | Olympio |

OTHER PUBLICATIONS

Wade et al., A Simulation Trial of Fiberoptic Assisted Coaxial Endotracheal Tube Exchange (FACETTE), Abstract and Slides, presented to the Joint Society for Technology in Anesthesia with International Meeting on Medical Simulation (IMMS), 2004, 14 pages.

Wade et al., Fiberoptic Assisted Coaxial Endotracheal Tube Exchange (FACETTE), presentation, presented to the Joint Society for Technology in Anesthesia with International Meeting on Medical Simulation (IMMS), 2004, 27 pages.

Extended European Search Report corresponding to European Patent Application No. 13864925.6 (8 pages) (dated Jul. 4, 2016).

International Search Report and Written Opinion, PCT/US2015/035953, dated Sep. 16, 2015.

* cited by examiner

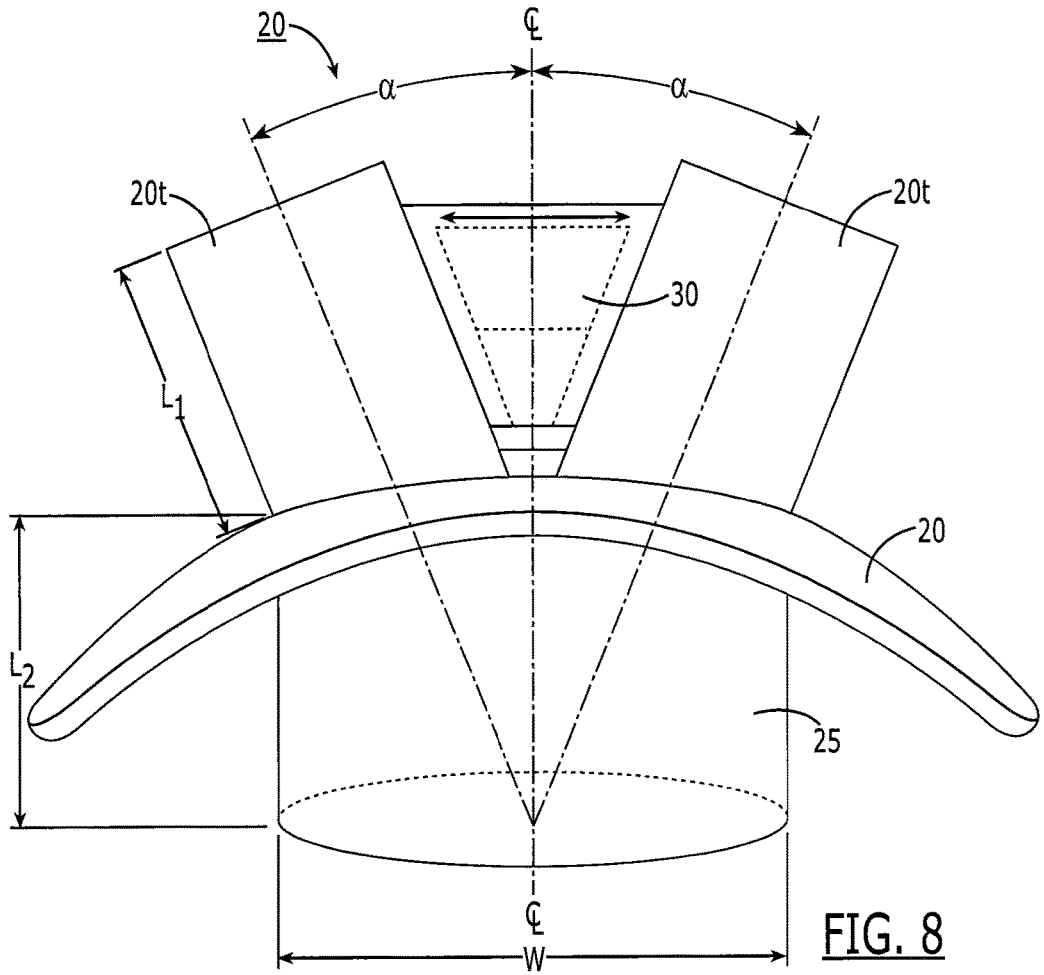
FIG. 8
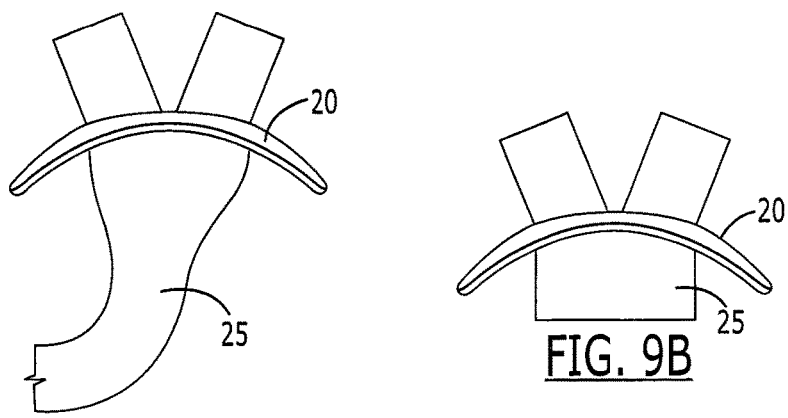
FIG. 9A
FIG. 9B

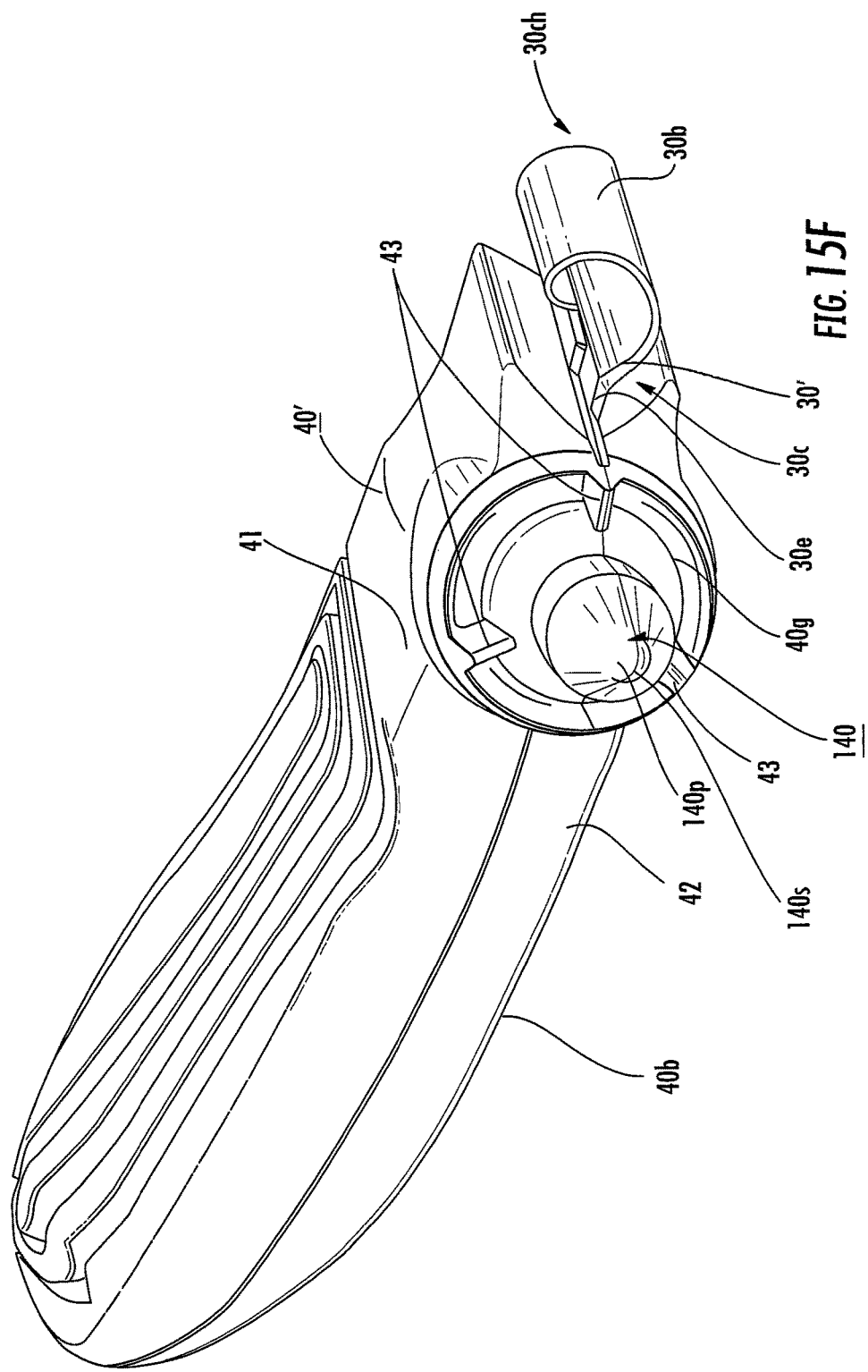

DEVICES THAT ALLOW FOR RAPID CHANGE OUT OF ENDOTRACHEAL (ET) TUBES AND RELATED METHODS

RELATED APPLICATIONS

This application is a continuation-in-part of U.S. patent application Ser. No. 14/104,481, filed Dec. 12, 2013, which claims the benefit of and priority to U.S. Provisional Application Ser. No. 61/738,583, filed Dec. 18, 2012, and U.S. Provisional Application Ser. No. 61/766,790, filed Feb. 20, 2013, the contents of which are hereby incorporated by reference as if recited in full herein.

FIELD OF THE INVENTION

The present invention relates to medical devices.

BACKGROUND

Endotracheal (ET) tubes are used to protect a patient's airway can and can sometimes be difficult to insert. An ET tube can be connected to a ventilator to help the patient breathe. Often, once the ET tube is in position, it remains in position and holds the patient's airway open. If the ET tube is prematurely removed or exchanged under adverse conditions, the airway can swell shut or become difficult to re-secure. Unfortunately, over time, the ET tube can be a pathway for bacteria or other undesired pathogens or may become somewhat occluded by biofilms or mucus or components. Also, the tube itself may undesirably change, e.g., the cuff may fail or the tube may change in size and/or shape which might require changing the tube, again sometimes under difficult circumstances.

SUMMARY OF EMBODIMENTS OF THE INVENTION

Embodiments of the present invention allow an endotracheal tube to be replaced (changed out) with stability while maintaining the patency of an airway under direct visualization of the internal trachea.

Embodiments of the invention are directed to tracheal tube devices. The devices include a mouthpiece with an external port merging into an open internal channel sized and configured to allow an endotracheal tube to extend therethrough into a trachea of a subject. The external port has a perimeter. The mouthpiece also includes at least one short tube with a cavity residing above the external port. The device also includes a handle holding a cutting member. The handle includes at least one interlock member that interlocks to the mouthpiece.

In an operative configuration, the handle can extend laterally away from the mouthpiece to position a distal end thereof at between 3-10 inches away from the mouthpiece. The handle interlock member can interlock to the at least one short tube. The cutting member can include a cutting blade that resides inward of a respective short tube to be positioned above but inside the perimeter of the external port.

The mouthpiece can have a monolithic molded body. An outerwall of the short tube can define a bounding surface of the perimeter of the external port.

The external port can have an elongate configuration with a width dimension greater than a length dimension. The short tube can reside proximate a medial segment of the width dimension. In use, the handle can be held by the short tube to be able to selectively and laterally extend to either a right or left side of a patient and/or in a caudal orientation to the patient.

The at least one interlock member can include a primary interlock member that projects a distance of between 0.25 inches and 4 inches below a bottom surface of the handle and can be slidably receivable into the cavity of the short tube. The cavity of the short tube can have a depth that is between about 0.25 inches and 4 inches.

The primary interlock member can be provided as first and second cooperating semicircular halves. A first half can be attached to the first handle member and the second half can be attached to the second handle member.

The cooperating semicircular halves can have flat inner surfaces that face each other.

The handle can include first and second cooperating handle members that can open and close relative to each other. The handle can hold a metallic member defining the cutting member between the first and second handle members. The metallic member can have a substantially cylindrical segment held by respective first and second spaced apart planar segments. The first planar segment can be attached to the first handle member and the second planar segment can be attached to the second handle member. In an operative configuration, the first and second handle members extend laterally away from the mouthpiece while the at least one interlock member resides in the short tube with the first and second planar segments being adjacent and parallel to each other with the cylindrical segment held over the external port of the mouthpiece.

The handle can include first and second cooperating handle members that can open and close relative to each other and that hold a metallic member defining the cutting blade therebetween and a pivotable latch member residing on one of the first and second members configured to latch and unlatch the first and second members.

The first and second handle members can have an outer upper surface, each with aligned raised pads. The latch can have a window that encases the aligned raised pads in a latched configuration.

The at least one short tube can be a single short tube. The short tube can have an outer rim with notches. The at least one handle interlock member can have a lower surface with a circumferentially extending groove and radially extending teeth. The groove can be configured to abut the rim of the short tube and the teeth can be configured to reside in respective notches.

The cutting member can be configured as a malleable unitary surgical metallic band that wraps together to define a longitudinally extending channel and a cutting edge.

Still other embodiments are directed to medical mouthpieces. The mouthpieces include an external port merging into an open internal channel sized and configured to allow an endotracheal tube to extend therethrough, the external port having a perimeter. The mouthpiece can also include a single short tube with a cavity residing above the external port. The mouthpiece can have a monolithic molded body and an outerwall of the short tube can define a bounding surface of the perimeter of the external port.

The external port can have an elongate configuration with a width dimension greater than a length dimension. The short tube can reside proximate a medial segment of the width dimension.

The cavity of the short tube can have a depth that is between about 0.25 inches and 4 inches.

The short tube can have an outwardly extending wall that tapers inwardly in a direction toward the external port of the mouthpiece into a smaller size.

The at least one short tube can be a single short tube.

Still other embodiments are directed to a medical device with a handle having first and second cooperating, laterally extending handle members. The laterally extending handle members can have a length that is between 3-10 inches and the handle members can open and close relative to each other. The handle can hold a metallic band defining a cutting blade between the first and second handle members.

The metallic band can have a (longitudinally extending) cylindrical segment that resides outside the first and second handle members.

The device can include a pivotable latch member residing on one of the first and second members configured to latch and unlatch the first and second members.

The device can include an interlock member that projects a distance of between 0.25 inches and 4 inches below the handle.

The interlock member can be provided as first and second cooperating semicircular halves, a first half can be attached to the first handle member and the second half can be attached to the second handle member.

Each of the cooperating semicircular halves can have flat inner surfaces that face each other.

The metallic band can have a longitudinally extending (substantially cylindrical) segment held by first and second spaced apart planar segments. The first planar segment can be attached to the first handle member and the second planar segment can be attached to the second handle member.

The first and second handle members can have an outer upper surface, each can also have aligned raised pads. The latch can include a window that can encase the aligned raised pads in the latched configuration.

The handle can include a lower surface with a circumferentially extending groove and radially extending teeth.

The teeth can have a V shape with a smaller end facing downward.

The metallic band can have a fenestrated configuration.

Embodiments of the invention are directed to tracheal tube devices. The devices include: (a) a mouthpiece sized and configured to allow an endotracheal tube to extend outwardly therefrom; and (b) a cutting blade in communication with an outwardly facing portion of the mouthpiece.

The mouthpiece can include at least one outwardly projecting substantially rigid short tube defining an open channel. The short tube can be configured to allow the endotracheal tube to slidably move therethrough.

The device can include a handle with first and second matably connecting members that attach together and hold the cutting blade and the handle can releasably engage the mouthpiece.

The mouthpiece can include spaced apart first and second short tubes, each defining an open channel. The device can further include a handle with an end portion that is sized to releasably engage a selected one of the at least one short tube so that, when attached to a respective short tube, the handle extends substantially orthogonally to a centerline of the attached short tube.

The mouthpiece can have a monolithic unitary body with an inwardly extending bite block and a pair of outwardly extending short tubes.

The short tubes can have axially extending centerlines that are spaced apart at an angle between 45 and 120 degrees at an outer end thereof.

The mouthpiece can include at least one outwardly extending substantially rigid short tube. The device can include a handle that holds the cutting blade and releasably engages the mouthpiece. The handle can also include a grip member that snugly holds an outerwall of an endoscope extending through the short tube inside the endotracheal tube. The short tube can have a slit that merges into a curved outer edge portion. The handle can have one end that is configured to reside against the short tube with an end portion residing in the curved outer edge portion of the short tube.

A cutting edge of the cutting blade can face the short tube with the endotracheal tube and endoscope residing in the short tube. The cutting blade can extend a distance of between about 0.1 inches to about 2 inches above an upper end of the short tube.

The mouthpiece can include at least one outwardly projecting substantially rigid short tube defining an open channel. The short tube can be configured to allow the endotracheal tube to extend outwardly therefrom (and be slidably removed or inserted via the channel of the tube). An outer end portion of the short tube can have (i) a first side with a curved end that merges into a downwardly extending slit and (ii) a second side with a substantially "V" shaped notch, with the open end of the V facing up.

The cutting blade can be configured as a malleable unitary surgical metallic band that wraps together to define a longitudinally extending (substantially cylindrical) channel that snugly encases an outerwall of an endoscope.

Other embodiments are directed to medical devices. The devices include: (i) a mouthpiece with at least one outwardly projecting substantially rigid short tube defining an open channel, wherein a respective short tube is configured to allow an endotracheal tube to extend outwardly therefrom; and (ii) a handle comprising a cutting blade configured to reside against the mouthpiece short tube so that the cutting blade resides adjacent the endotracheal tube extending therefrom with the cutting blade extending a distance above the mouthpiece short tube.

The handle can include a grip member configured to engage an endoscope residing inside the endotracheal tube at a location above the respective short tube.

The cutting blade can be a surgical metal band that has a cylindrical channel that snugly abuts an endoscope residing inside the endotracheal tube at a location above the respective short tube.

The mouthpiece can include spaced apart first and second short tubes, each defining an open channel. When in operative position, the handle can extend substantially orthogonal to a centerline of the attached short tube.

The mouthpiece can have a monolithic unitary body with an inwardly extending bite block and the at least one substantially rigid short tube can be a pair of spaced apart outwardly extending short tubes. The short tubes can have axially extending centerlines that are spaced apart at an angle between 45 and 120 degrees at an outer end thereof.

The handle can include first and second matably attachable components that position the grip member proximate to but above the short tube.

The at least one short tube can have a slit that merges into a curved outer edge portion. The handle can be configured to reside against the short tube with a portion residing in the curved outer edge portion of the short tube.

A cutting edge of the cutting blade can face the short tube with the endotracheal tube and endoscope residing therein. The cutting blade can extend a distance of between about 0.1 inches to about 2 inches above an end of the short tube.

Still other embodiments are directed to methods of changing respective endotracheal tubes. The methods include: (a) cutting an exposed portion of an endotracheal (ET) tube extending out of patient at an angle; then (b) pulling the endotracheal (ET) tube out of patient through a mouthpiece while the mouthpiece is in position on a patient with an endoscope extending therethrough, wherein the mouthpiece includes or is in communication with a cutting blade; (c) cutting a slit in the wall of the ET tube based on the pulling step; (d) removing the ET tube from the patient; then (e) inserting a different ET tube in the patient over the endoscope after the cutting while the mouthpiece remains on the patient, allowing change out of the ET tube while (i) maintaining visualization through the endoscope of a carina at a distal end of the trachea that splits to right and left lung bronchi and concurrently (ii) maintaining direct access within the trachea during the exchange process to thereby provide a clinician reassurance that access and pathway will not be compromised during the exchange.

The method can include, before the cutting, attaching a handle to the mouthpiece. The handle can have a cutting blade and the attaching can be carried out to position a cutting edge of the cutting blade adjacent an outerwall of the ET tube.

The cutting can be carried out to occur proximate to but above the short tube of the mouthpiece.

The pulling can be carried out by attaching forceps to the ET tube at a top portion of a short tube or above the short tube of the mouthpiece and pulling the ET tube at an angle with respect to the short tube to split the ET tube as it contacts the cutting blade. The removing and inserting steps can be carried out in under 1 minute.

The cutting blade can be defined by a malleable surgical metal band that wraps together to define a cylindrical channel. The method can include placing the metal band about an outerwall of an endoscope so that the endoscope resides snugly in the cylindrical channel.

The device can also be called an "endotracheal tube exchanger" that can be used in conjunction with a fiber optic bronchoscope (i.e., endoscope) and can allow a physician to (a) directly maintain visualization of the internal airway as the old tube is cut and removed, (b) slide the new endotracheal tube into place quickly and confidently, (c) maintain stability and avoid injury, (d) optimize depth of the new tube, and (e) deliver oxygen substantially or even entirely throughout the entire exchange.

The handle with cutting member can be single-use disposable. Alternatively, the handle can be re-useable (after sterilization) and the cutting member or blade can be single use disposable.

The device can include a slicing tool handle that securely fastens the fiber optic scope for the slicing/cutting of the endotracheal tube being removed and includes an oral (mouthpiece) interlocking stabilizer that protects the patient and physician against the force of cutting and exchange.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

Other systems and/or methods according to embodiments of the invention will be or become apparent to one with skill in the art upon review of the following drawings and detailed description. It is intended that all such additional systems, methods, and/or devices be included within this description, be within the scope of the present invention, and be protected by the accompanying claims.

BRIEF DESCRIPTION OF THE DRAWINGS

Other features of the present invention will be more readily understood from the following detailed description of exemplary embodiments thereof when read in conjunction with the accompanying drawings.

FIG. 8 is an enlarged view of an exemplary mouthpiece suitable for use with the tracheal assembly according to embodiments of the present invention.

FIGS. 9A and 9B are side section schematic illustrations of different exemplary configurations of internal (bite block) configurations for the mouthpieces described herein.

FIG. 15F is a side, bottom perspective view of the handle shown in FIG. 15A.

DETAILED DESCRIPTION OF EMBODIMENTS OF THE INVENTION

Figure 1:
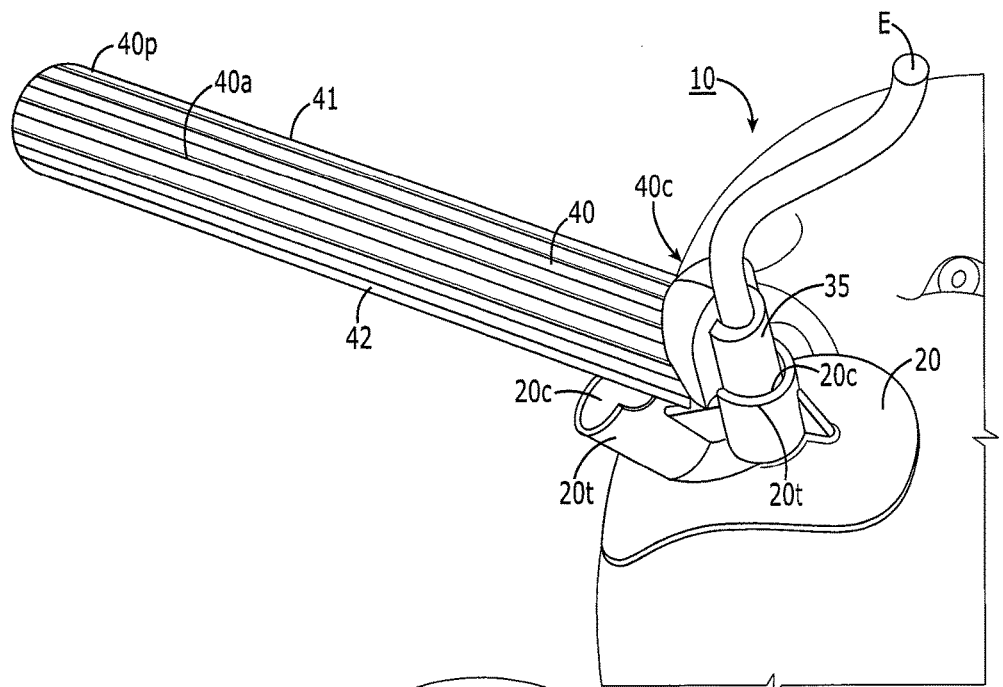
FIG. 1 is a bottom side perspective view of a tracheal assembly according to embodiments of the present invention.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise. One or more features shown and discussed with respect to one embodiment may be included in another embodiment even if not explicitly described or shown with another embodiment. The abbreviations of "FIG." and "Fig." are used interchangeably with the word "Figure" in the application and drawings.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal", "cephalad", "caudal", "inferior", "superior" and the like are used herein for the purpose of explanation only unless specifically indicated otherwise.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise. In the claims, the word "a" with respect to an element is intended to include one or more of such elements and is not limited to a single such element unless stated otherwise.

The term "about" means that the recited number or value can vary by +/−20%.

The term "sterile" means that the noted device or material meets or exceeds defined medical guidelines of cleanliness and is substantially (if not totally) without contaminants so as to be suitable for medical uses.

The term "short tube" refers to a tube attached or integral to a mouthpiece that has a length that is between about 0.25 inches to about 4 inches, more typically between about 1 to about 2.5 inches.

Embodiments of the invention are particularly suitable for human or animal use.

Figure 2:
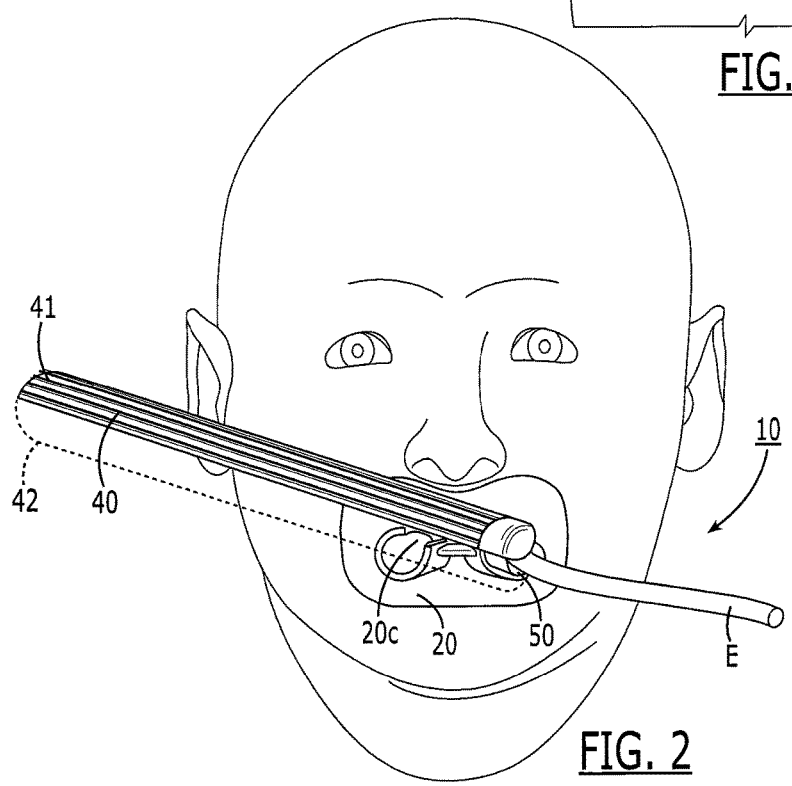
FIG. 2 is a front perspective view of the device shown in FIG. 1, without one (the lower) side of the handle according to embodiments of the present invention.
Figure 3:
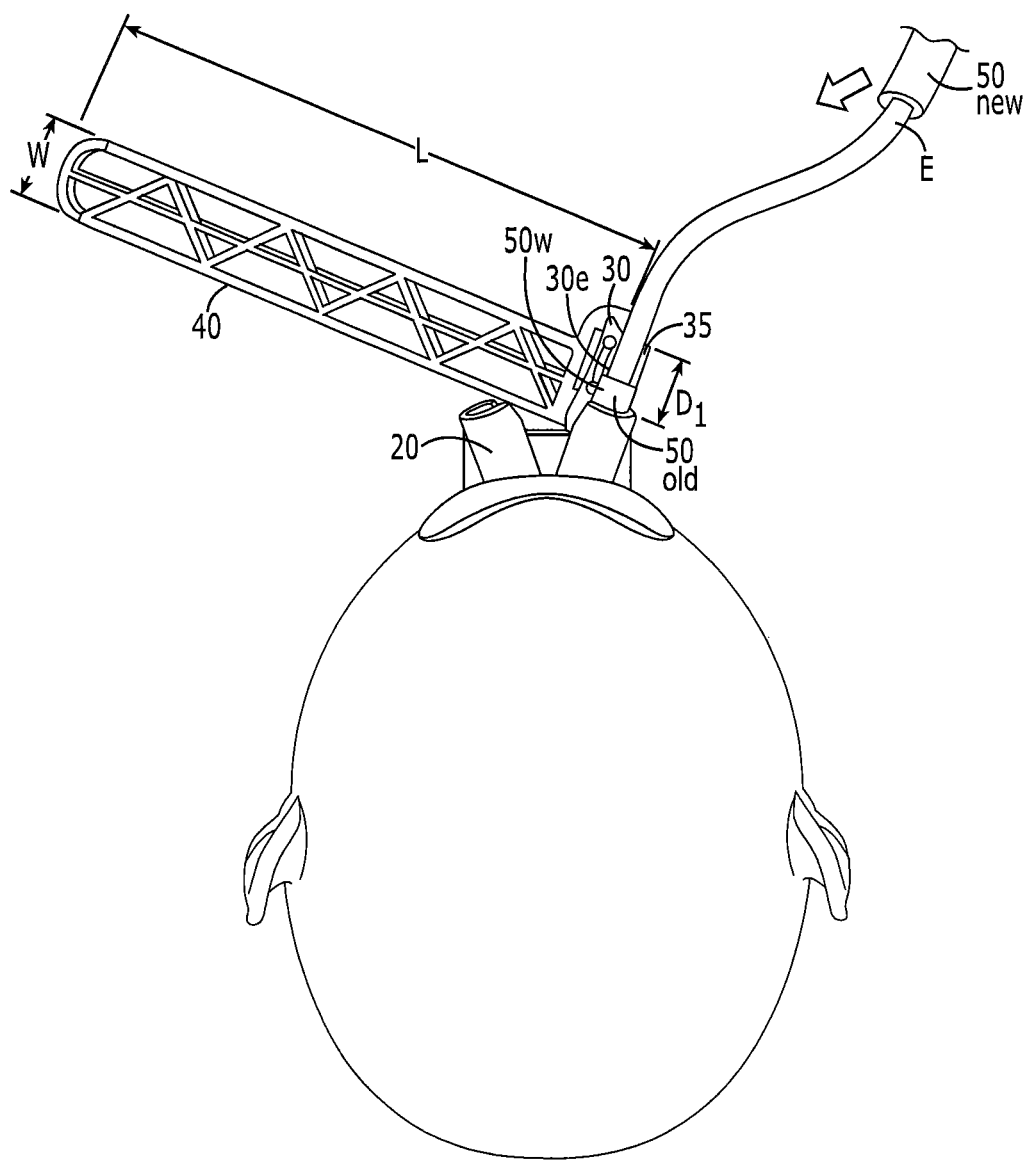
FIG. 3 is a bottom perspective view of the device shown in FIG. 2 according to embodiments of the present invention.

Turning now to the figures, FIGS. 1-3 illustrate one embodiment of a tracheal assembly 10. As shown, the tracheal assembly 10 includes a mouthpiece 20. The mouthpiece 20 defines at least one access channel 20c that can slidably receive an endotracheal (ET) tube 50. The device 10 includes a cutting member 30 that is sized and configured to cut into an outer wall 50w of the ET tube 50 proximate the mouthpiece 20 as the tube 50 is slidably removed from a patient. The cutting member 30 can have any suitable configuration but is typically a flat razor or scalpel. The term "cutting blade" is used interchangeably with "cutting member" and is used broadly to include any member having at least one cutting edge or surface. Other characteristics of the cutting blade 30 may include one or more of an appropriate tensile strength, shape memory material, razor-sharpness, stiffness, resistance to twist or torque and the like.

Typically, the mouthpiece channel 20c concurrently receives both the ET tube 50 and an endoscope E (i.e., "bronchoscope") that extends into the trachea of the patient within the ET tube. The cutting blade 30 orients its cutting edge 30e (FIG. 3) into/over the channel 20c to be able to cut into a wall 50w of the adjacent ET tube 50 as the ET tube is pulled from the patient over the endoscope E.

Figure 4A:
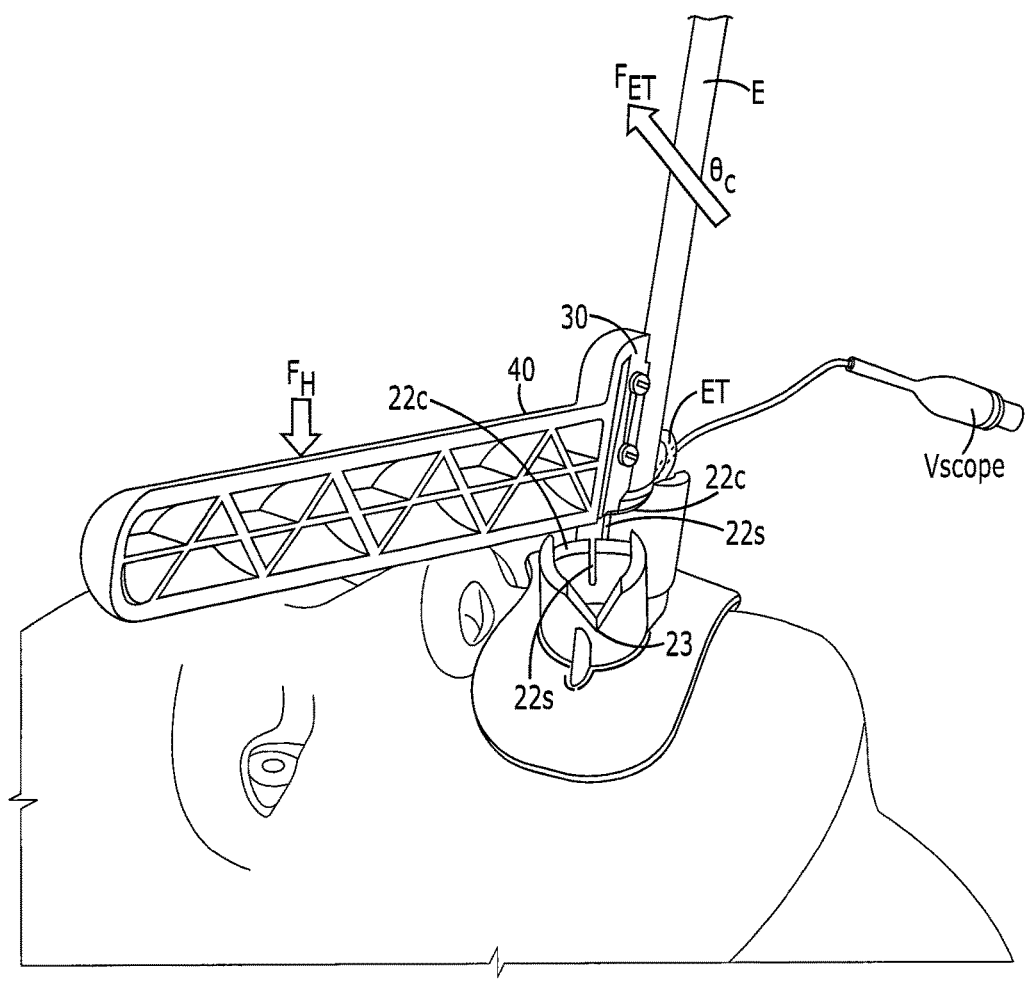
FIG. 4A is a side perspective view of another embodiment of the tracheal assembly device according to embodiments of the present invention.
Figure 4B:
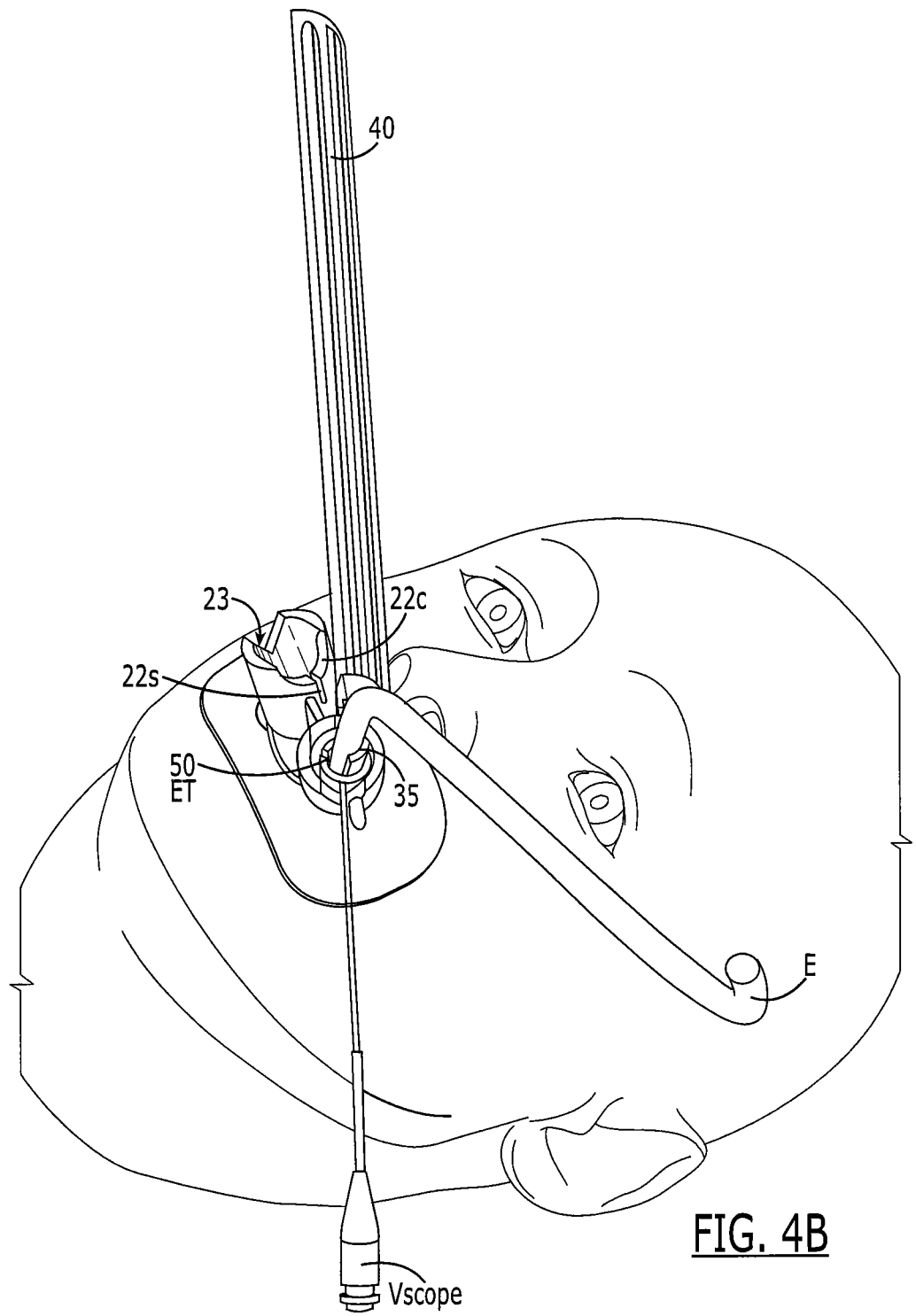
FIG. 4B is an opposing side perspective view from that shown in FIG. 4A.
Figure 6:
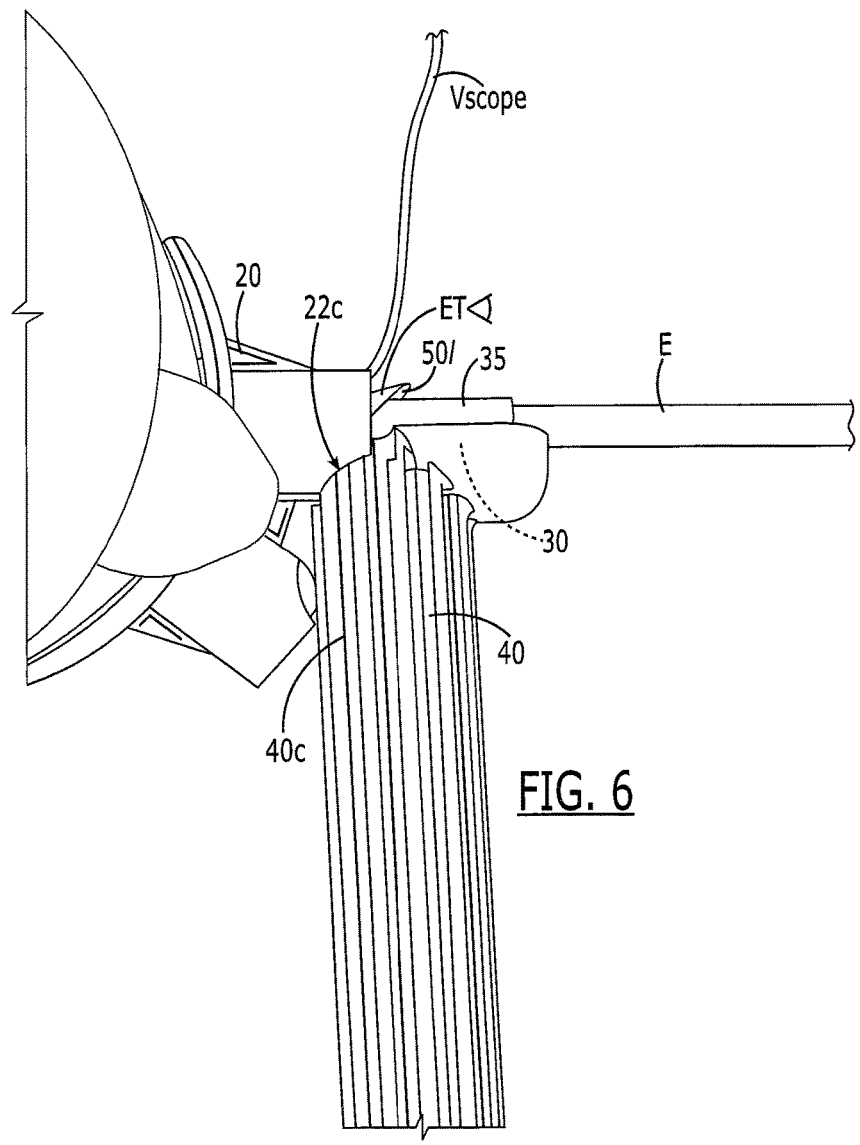
FIG. 6 is a top perspective view of the device shown in FIG. 4A according to embodiments of the present invention.
Figure 7A:
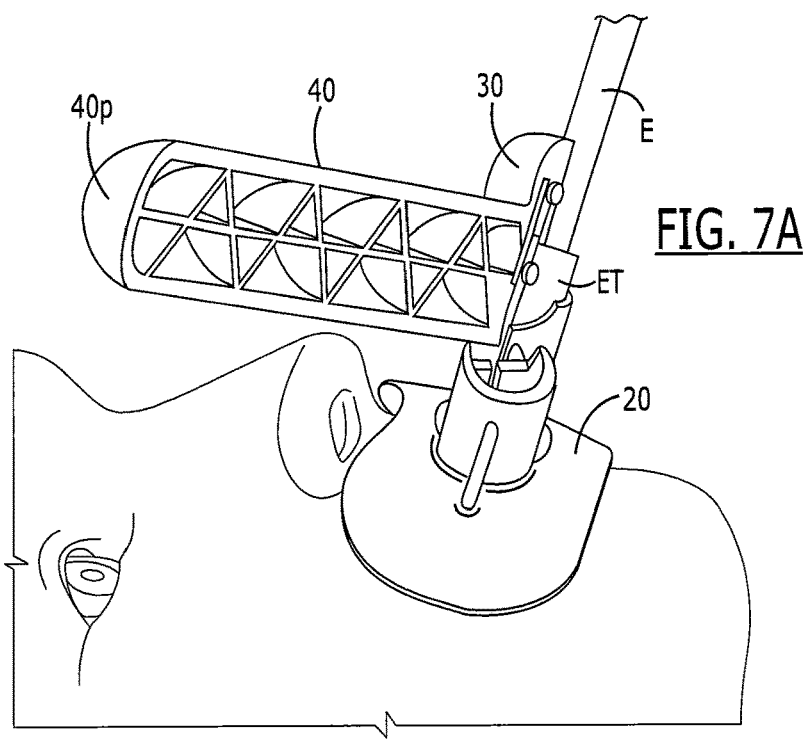
FIG. 7A is a patient right side perspective view of a tracheal assembly similar to that shown in FIG. 4 illustrating the mouthpiece having a different short tube configuration according to embodiments of the present invention.
Figure 7B:
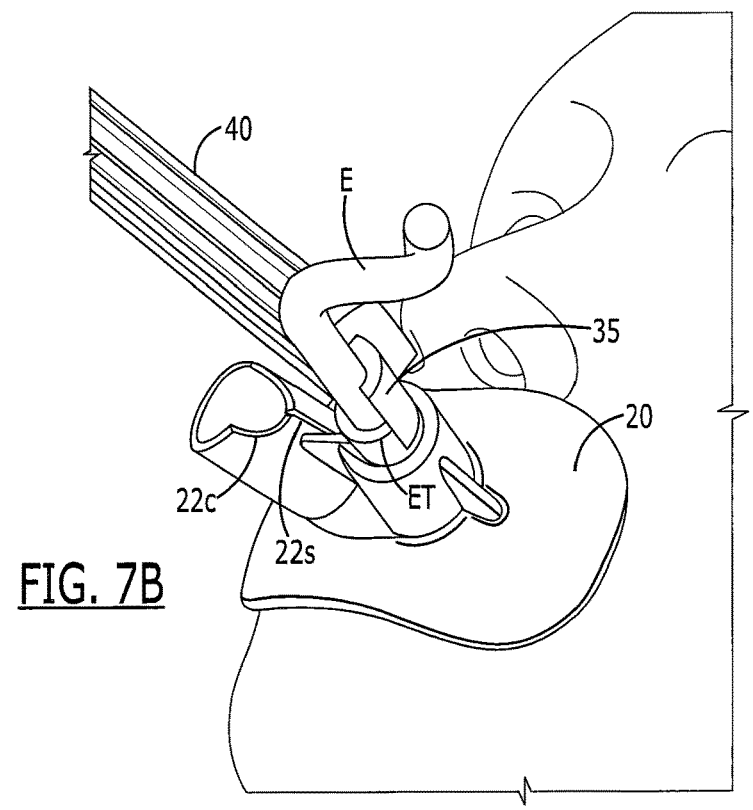
FIG. 7B is a patient left side perspective view of the tracheal assembly shown in FIG. 7A.

The endoscope E can (and should) remain in position in the patient during the change out of the ET tubes. As shown in FIG. 3, a new ET tube 50new can reside on the endoscope E above the "old" ET tube 50old that is being replaced so that the new tube 50new can be slid down over the endoscope E (which acts as a stylette or guidewire), typically after the handle 40 (where used) is at least partially removed so as to not occlude the travel path to position the new tube properly in the patient once the old tube 50old has been removed from the patient. FIGS. 4A, 4B and 6 illustrate that a viewing scope lead (Vscope) can also be in position during the procedure.

FIGS. 1-3, for example, show that the device 10 can include a handle 40 that can engage the mouthpiece 20. However, a user may directly apply force to the mouthpiece or to a grip member that holds the endoscope E, which may not require the use of a handle 40.

However, in particular embodiments, the handle 40 is typically configured to releasably engage the mouthpiece 20. However, in some embodiments, the handle 40 can be permanently attached to the mouthpiece. Referring to FIG. 3, the handle 40 can have any suitable laterally extending (in a direction away from the mouthpiece) length "L" but is typically between 2-10 inches, more typically between 3-10 inches, such as about 3 inches, about 4 inches, about 5 inches, about 6 inches, about 7 inches, about 8 inches, about 9 inches or about 10 inches. The handle can have a width "W" that is between about 0.25 inches to about 2 inches, typically about 1 inch. As shown in FIG. 1, the handle 40 can have an elongate primary body (arm) 40a with an arcuate profile 40p when viewed from the end and may also have a distal end that is substantially orthogonal to the arm 40a which has a semi-circular curved shape 40c.

The mouthpiece 20 can have a substantially rigid or semi-rigid monolithic body. The mouthpiece 20 can alternately comprise components that snap together or apart, such as components that reside on either side of the short tube 20t (where used) or channel 20c to provide a seam about the channel 20c for easy installation or removal about a respective ET tube thereat.

In operation, a user can push down on the handle 40 to apply a force $F_H$ (FIG. 4A) while the ET tube 50 is pulled out. The ET tube is typically pulled out by the same clinician (e.g., doctor or nurse) applying the extraction force $F_H$ but a cooperating different clinician may also pull the old ET tube out. The person withdrawing the old tube 50 can use fingers and/or forceps to attach to and pull the "old" ET tube 50 upward with a force direction $F_{ET}$ to slit the outer wall 50w of the respective tube using the cutting blade 30 to remove the old tube 50 while the endoscope E remains in position. The person removing the tube 50 can use a pulling direction that is at an angle θc that is toward the cutting blade 30 (toward the handle in the configuration shown in FIGS. 1-4, for example).

Figure 5:
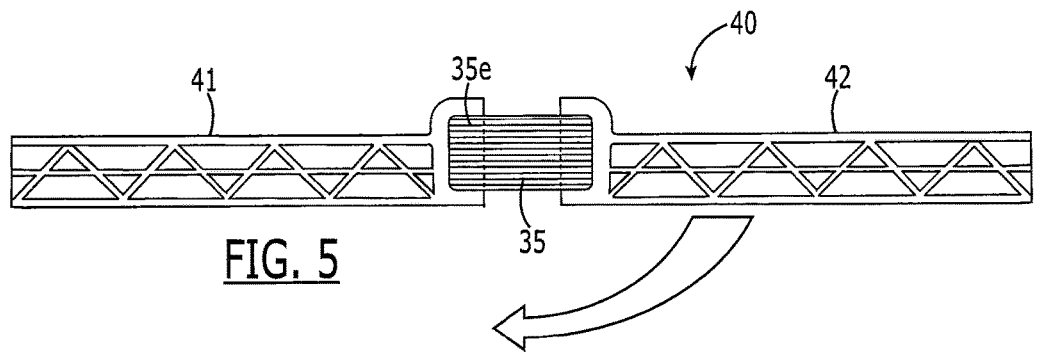
FIG. 5 is a schematic illustration of an exemplary configuration of a handle according to embodiments of the present invention.

As shown in FIGS. 1 and 5, the handle 40 can have first and second matably attachable elongate members 41, 42 that can attach together before or after one or both are attached to the mouthpiece 20. In other configurations, the handle 40 has a single piece body.

The device 10 can optionally also include a grip member 35 that snugly attaches to the endoscope E to hold the endoscope E in position (and substantially if not totally stationary) in response to the holding force $F_H$ being applied while a clinician pulls the old tube 50old up to remove it from the patient. Typically, the grip member 35 extends out from a distal end of the handle 40d. The grip member 35 can be a flexible (e.g. polymeric or rubber) strap with opposing sides held by distal end portions 40d of the different handle members 41, 42. The grip member 35 can have any suitable length but is typically between about 0.25-2 inches such as between about 0.5 to about 1 inch, including, for example, about 0.8 inches in some embodiments. A user can also or alternatively manually directly hold the endoscope E or use other devices for same.

FIG. 5 illustrates that the grip member 35 is held by the distal end portions of the handle members 41, 42. In use, a user can wrap the grip member 35 about the endoscope E, then close the members 41, 42 together (typically via snap fit or other frictional engagement) to hold the endoscope E snugly inside the grip member 35. One or both ends of the grip member 35 can be pulled to tighten the hold (and/or adjust the grip member length). However, other grip member configurations can be used. For example, the grip member 35 can be directly mounted to the mouthpiece 20 instead of the handle 40 or can comprise cooperating components that are held by both the handle 40 and mouthpiece 20. The grip member 35 can be configured as a clamp or a molded plastic or semi-rigid polymeric member that is scored with geometric shapes so as to be able to bend about the endoscope E. The grip member 35 can be provided as a separate member that releasably attaches to the handle or is used by a clinician separate from the mouthpiece or handle. The grip member 35 can reside partially about the outer wall of the endoscope or entirely as shown in FIG. 6, for example.

As shown in FIGS. 3 and 4A, for example, the cutting blade 30 can reside in the handle 40 so that, when in position, a cutting edge 30e of the cutting blade 30 faces into the channel 20c to be able to cut into the outer wall 50w of the adjacent ET tube 50 as the ET tube is pulled from the patient over the endoscope E. However, it is contemplated that the cutting blade 30 can reside in other locations and/or have other configurations. For example, the cutting blade 30 can be retractable/extendable by a user rather than in a fixed location. FIG. 8 illustrates that the cutting blade 30 can reside on the mouthpiece 20 and can be configured to slide, rotate, pivot or otherwise deploy laterally into a channel 20c that holds the ET tube 50. In this embodiment, the cutting blade 30 can reside in a protective sheath or housing for safety. Where short tubes 20t are used, they can include longitudinally extending slits, slots or other access channels aligned with the cutting blade 30, so that when deployed laterally from a home position, the cutting blade 30 can extend into the tube 20t a distance sufficient to cut the outer wall 50w.

The mouthpiece 20 can be a molded monolithic body with one or more integral short tubes 20t. Alternatively, other channels and channel members can be used. In some embodiments, a short tube 20 can be matably securely attached in situ to a port or channel in the primary mouthpiece body. The short tube 20t can threadably attach, adhesively attach or snap-fit into a recess/channel in the mouthpiece body, for example.

The mouthpiece 20 can be configured for use as an ET tube holder that can include a locking clip for secure tube position and/or as a modified conventional biteblock for endoscopy. Thus, the mouthpiece 20 can be placed on the patient during the initial ET tube insertion procedure. Alternatively, the mouthpiece 20 can be a special purpose mouthpiece 20 that is used only during a replacement or change out ET tube procedure.

As shown in FIGS. 1-8, the mouthpiece 20 includes two spaced apart channels 20c provided by two short tubes 20t. During an ET tube replacement or change out procedure, a user can select which channel 20c (i.e., the right or left) to use, depending on user preference (which side of the patient they may reside on and/or whether the user is right or left-handed). In other embodiments, the mouthpiece 20 can have a single channel 20c (FIG. 10) and this single channel can be medially located on the mouthpiece or positioned to one side closer than the other.

As shown in FIGS. 4A and 6, for example, the handle 40 can have a distal end portion that has a curved outwardly projecting (semicircular or arcuate) shape 40c that is matably received in a substantially matably curved (semi circular) recess 22c residing in the upper (outer facing) end. The arcuate recess can have a radius of curvature that is between about 0.2 to about 0.5 inches, but other shapes and sizes of matable configurations may be used. The short tube(s) 20t can also optionally include an elongate slit 22s that resides under the curved recess 22c. The slit 22s can merge into the curved recess 22c and may allow the cutting edge 30e of the blade 30 to enter therein.

The cutting blade 30 can be configured to extend a short distance above the uppermost end of the short tube 20t, where used, typically between 0.1 to about 0.5 inches, more typically about 0.25 inches.

As shown in FIGS. 4A and 4B, the short tube 20t can also or alternatively include an outer edge with a notch 23 such as a "V" shaped notch on a side that is diametrically opposed from the curved recess 22c. FIG. 1 illustrates the mouthpiece 20 without this feature. In use, a clinician may place forceps against the ET tube 50 to pull the old tube 50 upward (and typically but not required, toward the blade 30). FIG. 6 illustrates that the indwelling endotracheal tube 50 can be cut at an angle to define a leading end 50l at a position that is proximate but above the mouthpiece 20, at initiation or just prior to start the removal process.

FIG. 8 illustrates that the short tubes 20t can have a length $L_1$ and can be spaced apart and angled so that, at the outer edges, the short tubes angle outward at an angle "a" that is between 15 to 45 degrees from vertical (also shown as the centerline C/L of an optional underlying biteblock 25). The short tubes 20t (where two are used) can angle outwardly at the same angle or at different angles. The short tube(s) may also be vertical. The short tubes 20t can have axially extending centerlines that are spaced apart from each other at an angle between 45 and 120 degrees at an outer end thereof.

The biteblock 25 can be substantially rigid or may be flexible or semi-rigid for patient comfort. The biteblock 25 can have a straight length $L_2$ that is between about 1-2 inches (for adults) and a width W that is between about 1.5 to about 2 inches (for adults). As shown in FIG. 9A, the biteblock 25 can have a radius of curvature that begins a distance inward of the external face-contacting surface of the mouthpiece, after the straight segment, for a distance such as about 1-2 inches (for adults) past the straight segment. FIG. 9B illustrates that the mouthpiece 20 can include only a straight biteblock 25.

Figure 10A:
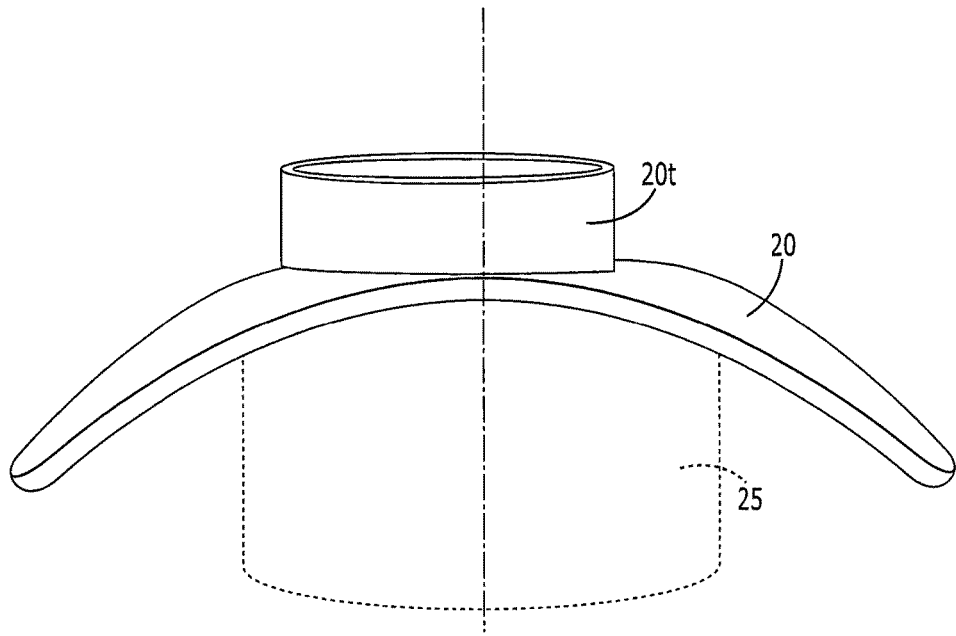
FIG. 10A is a side schematic illustration of a mouthpiece with a different configuration according to embodiments of the present invention.

FIG. 10A illustrates that the mouthpiece 20 can include a single short tube 20t and it may be substantially vertical or angled as described above with respect to the dual short tube configurations such as shown in FIG. 8.

Figure 10B:
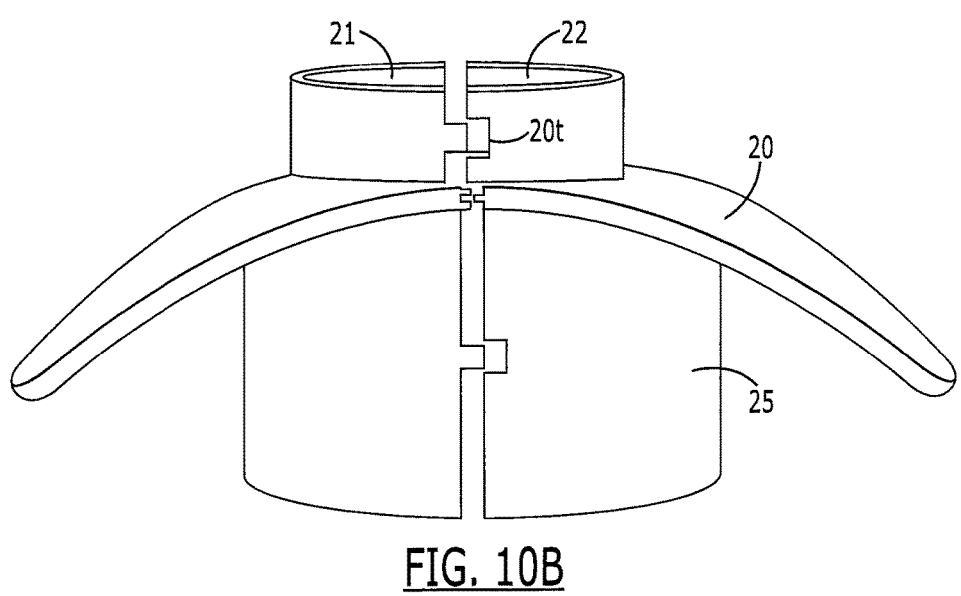
FIG. 10B is side schematic illustration of a mouthpiece with matably attachable components according to embodiments of the present invention.

FIG. 10B illustrates that the mouthpiece 20 can comprise matably attachable members 21, 22 that can be attached in situ about an indwelling ET tube 50 according to particular embodiments of the present invention.

Figure 11:
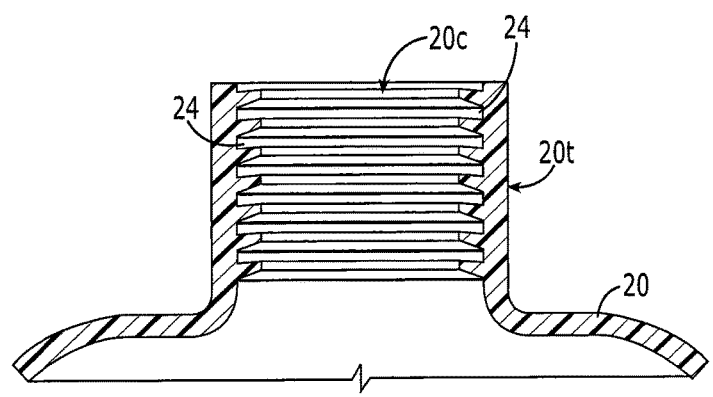
FIG. 11 is a lateral section schematic illustration of an external short tube of the mouthpiece according to embodiments of the present invention.

FIG. 11 illustrates an exemplary interior surface modification of a channel 20c to facilitate tight connection with the ET tube 50 and alignment with a cutting blade 30. The surface modifications shown include resilient fingers but other friction enhancing configurations that still allow for sliding of the ET tube 50 may be used including, for example, coatings, embossed surfaces and the like or combinations of the above.

Figure 12B:
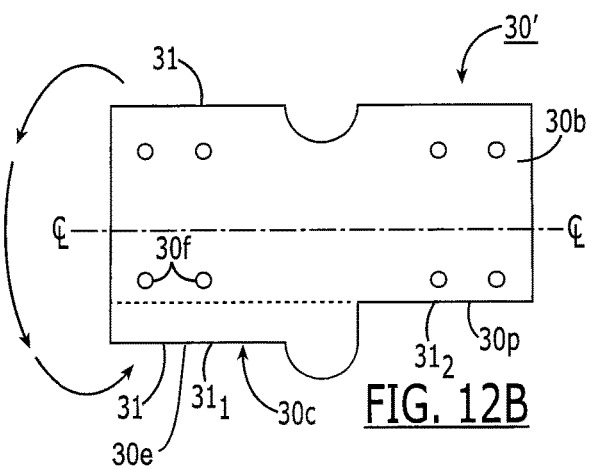
FIG. 12B is a side view of an exemplary cutting band that is used to form the cooperating cutting member of the tracheal assembly shown in FIG. 12A.
Figure 12A:
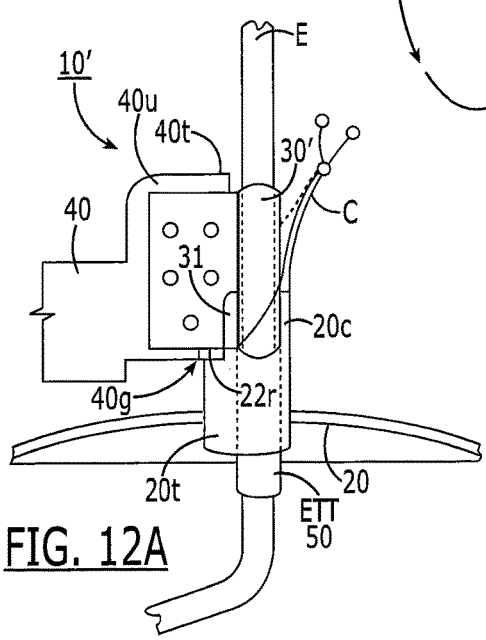
FIG. 12A is a schematic illustration of another embodiment of a tracheal assembly according to embodiments of the present invention.
Figure 12C:
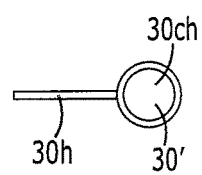
FIG. 12C is a top view of the cutting band shown in FIG. 12B in a formed configuration.

FIGS. 12A-12C illustrate another embodiment of the tracheal assembly 10. As shown in FIG. 12A, the tracheal assembly device 10 includes a mouthpiece 20 with at least one open channel 20c and tube or post 20t that cooperates with a cutting blade 30' held by a handle 40. The top of the handle 40t can be sized and configured to abut against the endoscope E. The cutting blade 30' can comprise a unitary, substantially rectangular-shaped band 30b of surgical grade metal, e.g., stainless steel, that can wrap around a particular size fiberoptic scope E. When wrapped around the scope E, the band 30b can tightly grasp the scope E and define a cylindrical channel 30ch (FIG. 12C). The band 30b can be formed in situ or prior to use (e.g., "pre-formed") to wrap about its long axis "L" to form the cylindrical channel 30ch.

In some embodiments, the band 30b comprise a thin, sufficiently strong, malleable metallic material such as a metal shape memory material. The band 30b can be provided pre-formed and sized for particular scopes. The band 30b can be formed in situ or on site corresponding to the scopes E at that facility and in use.

The band 30b can also have other shapes. Non-cutting edges may be coated with a protective (spongy, foam-like material, rubber or other) material to inhibit user exposure to sharp edges.

In position, one or both of the two trailing sides 31, typically only one of the trailing sides 31 emanating from the scope E forms the cutting edge 30e as a flat cutting edge surface 30c, extending between about 2-10 mm from the scope edge. The two long sides of the band 30b can have a length sufficient to continue upward another 10-40 mm, typically about 20 mm, each side firmly anchored to each half of the handle 40. As shown in FIG. 12B, one long side of the band 30b can have a first segment $31_1$ that extends a further distance down (relative to the orientation shown) than a second segment $31_2$. The first segment $31_1$ defines the flat cutting edge 30c/30e.

The handle 40 can include two matable halves that can be configured to have a releasable engagement with the cutting band 30b and can have secure-alignment features 40f with the band alignment feature 30f (e.g., male-female features, pins/holes and the like), so that a clinician can effect substantially instant or quick release of the two halves after cutting is complete. As shown in FIG. 12C, the band 30b, when wrapped, includes a planar length 30h of fastening surface that attaches to the handle 40.

The semi-circular distal and inferior end of the cutting handle 40 can have groove 40g which snugly mates with a rim 22r of the short tube 20t. The upper part of the distal handle 40u that secures the cutting band 30b can be configured to closely approximate the cylindrical channel 30ch, nearly touching the scope E. The inferior part of the distal handle can be notched to expose the cutting edge 30c of the metal band 30b, and the superior portion of the notch can form a V to facilitate ETT 50 separation upon extraction as it is cut away.

In this embodiment, the inner rim 22r of the tube 20t is not required to have a vertical slit for any cutting blade and there is no longer any inferiorly-protruding cutting blade (such as the cutting blade 30 from the embodiments shown with respect to FIGS. 3 and 4A). A lateral portion of the post or tube 20t can have an open window or side 20a that allows physical access to the ET tube to facilitate grasping the ET tube with the clamp C (e.g., a Kocher Clamp, hemostat and the like).

The cutting band 30b can be precision cut/sized according a corresponding (exact or within some tight tolerance) size (thickness/diameter) of the fiberoptic scopes E on hand at any institution. The cutting band 30b can accommodate a range of scopes E from thin to thick scopes (e.g., 5.3 mm, 5.7 mm, 6.0 mm diameters). Alternately, model/size-specific bands 30b can be provided. The bands 30b can be provided in different sizes as a kit for selection onsite to match an endoscope in use.

Embodiments of the invention can be carried out to maintain visualization (through the endoscope) of the carina (the distal end of the trachea that splits to right and left lung bronchi), while concurrently and also maintaining direct access within the trachea during the exchange process. This combination gives the clinician the reassurance that access, depth, stability, and pathway will not be compromised during the exchange.

Thus, the invention fills a long felt need that addresses the deficiencies and problems in conventional exchanges which could be frightening and dangerous, particularly in swollen or obese patients, or those with otherwise difficult intubations. In the past, typically, the old tube must be pulled out blindly over an exchange rod, tube, stylette or bougie, and then the new tube is slid over the bougie blindly and without stability. One may lose access to the trachea as the rod, tube or bougie, inadvertently, slides in/out, or kinks into the esophagus, or it may go in too far and puncture the bronchus, or might go through the ET tube Murphy eye.

Thus, the methods and devices contemplated by embodiments of the invention are configured so that the pathway is not lost and the sight of the pathway inside the trachea during the exchange is maintained.

It is contemplated that such tubes can be changed out as needed for malfunction or for size change, or on any schedule deemed appropriate by medical care.

In some embodiments the procedure can be carried out as follows. The mouthpiece 20 is in place or put in place (threaded or slid over) the indwelling ET tube 50, after removing the ET adaptor, allowing the ET tube to protrude from hole 20c (where different channel options are provided, a user can select the channel to accommodate left/right handed users and/or to allow the procedure to be done from the other side of the patient). A new ET tube is (previously) preloaded onto a long endoscope. Then the handle 40 with cutting blade 30' of formed band 30b (FIGS. 12A-12C, 14) can be wrapped around the shaft of the bronchoscope between the two ET tubes. Then the old ET tube 50old is grabbed with a clamp or forceps after removal of the ET tube adaptor. The endoscope is then pushed through the old indwelling ET tube (so the endoscope has the ne and the old ET tubes on it). The handle 40 is anchored to the mouthpiece tube 20t. Then the old ET tube is pulled up. As it is pulled up, it is slit open longitudinally by the cutting blade 30, so that the old ET tube peels off the endoscope, to the side. During this time, the endoscope is still securely in the patient's airway providing direct continuous visualization of the carina by the clinician. Then, the handle 40 is removed and the new ET tube 50new (which has been at the top of the endoscope this whole time) is slid down the endoscope E and into the airway, as it would be during any typical and common fiberoptic intubation.

It is noted that where the embodiment of FIG. 3 or 4A, for example, are used, the handle 40 and grip 35 can be positioned in lieu of or with the wrapped band 30b so that the cutting blade 30 contacts the old ET tube 50old.

Figure 13:
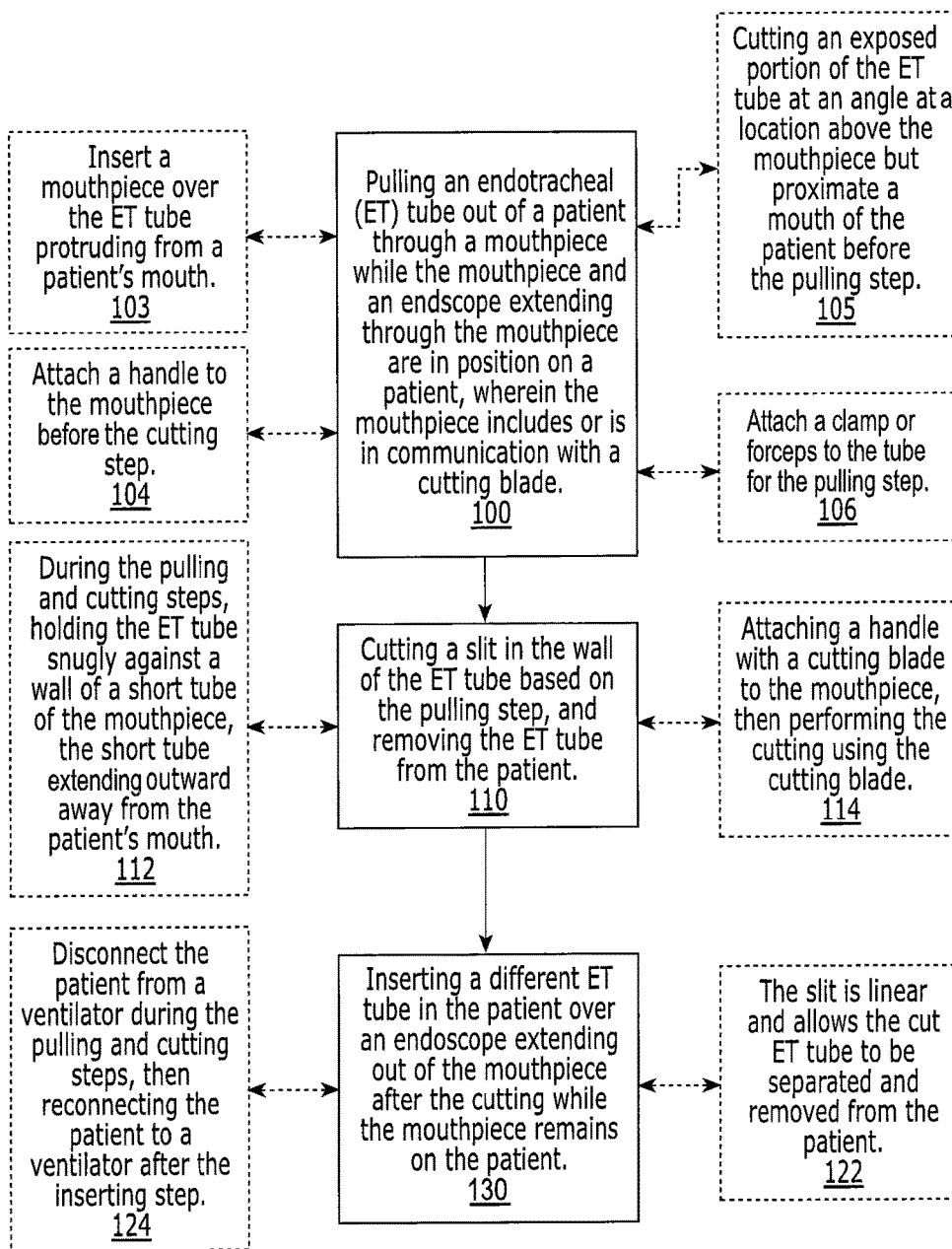
FIG. 13 is a flow chart of exemplary operations that can be used according to embodiments of the present invention.

FIG. 13 illustrates exemplary steps that can be used to rapidly remove and replace an endotracheal tube (typically in under about 1 minute). An endotracheal (ET) tube can be pulled out of patient through a mouthpiece while the mouthpiece and an endoscope extending through the mouthpiece are in position on a patient, wherein the mouthpiece includes or is in communication with a cutting blade (block 100). A slit can be cut in the wall of the ET tube based on the pulling step and removing the ET from the patient (block 110). A different ET tube is inserted over the endoscope into the patient after the cutting while the mouthpiece remains on the patient (block 130).

The mouthpiece can be inserted into the patient's mouth over an indwelling ET tube protruding from a patient's mouth (block 103). A handle can be attached to the mouthpiece before the cutting step (block 104).

An exposed portion of the ET tube can be cut at an angle at a location above the mouthpiece but proximate the mouth before the pulling step (block 105).

Forceps can be attached to the ET tube for the pulling step (block 106).

During the pulling and cutting steps, the ET tube can be snugly held against a wall of a short tube of the mouthpiece, the short tube extending outward away from the patient's mouth (block 112).

The patient can be disconnected from a ventilator during the pulling and cutting steps, then reconnected after the inserting step (block 124). A handle with a cutting blade can be attached to the mouthpiece, then the cutting can be performed using the cutting blade in the handle (block 114). The slit can be linear and allows the cut ET tube to be separated and removed from the patient (block 122) while the endoscope remains in position.

Figure 14:
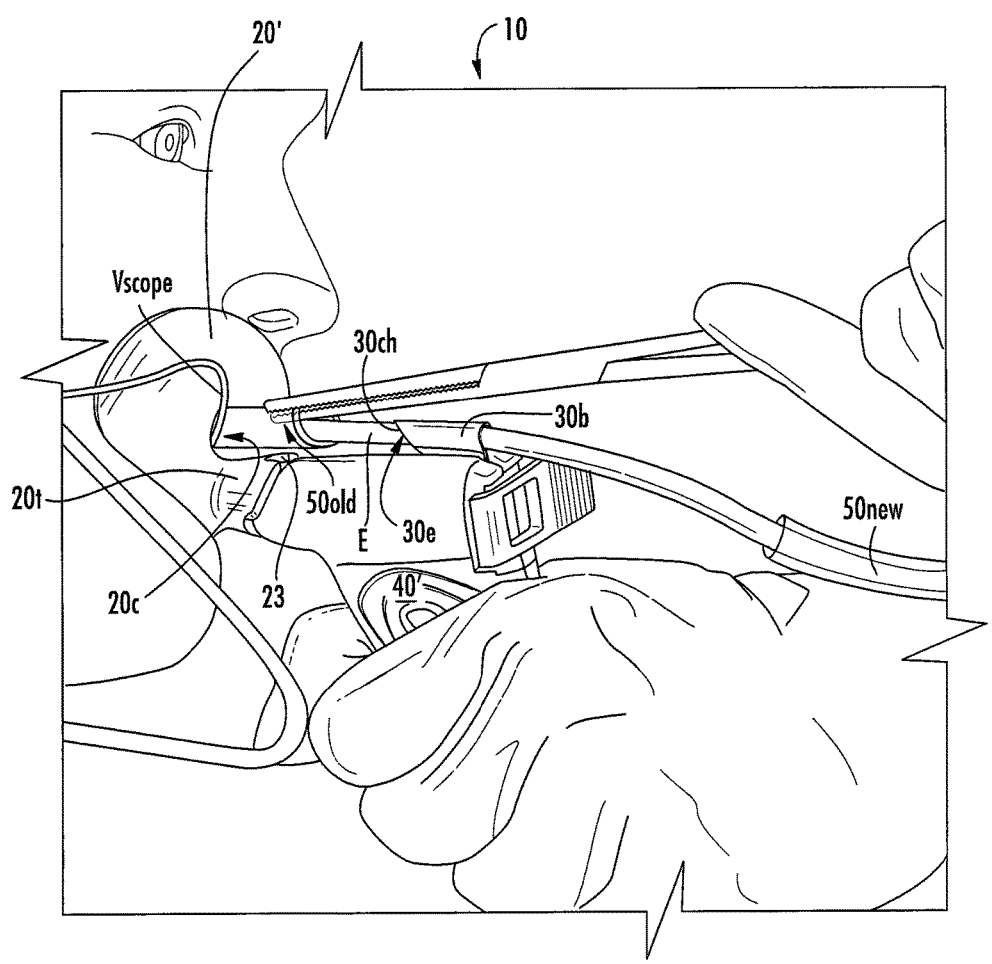
FIG. 14 is a side perspective view of another embodiment of the device in position on a (phantom) patient according to embodiments of the present invention.

FIG. 14 illustrates another embodiment of the endotracheal device 10. In this embodiment, similar to the embodiment described with respect to FIGS. 12A-12C, the handle 40' holds the cutting blade 30' (i.e., band 30b), typically in a partially or totally closed longitudinally extending channel 30ch, e.g., a substantially cylindrical channel 30ch, and the handle 40' can interlock with the short tube 20t of the mouthpiece 20'. In this embodiment, the short tube 20t that interlocks with the handle 40' can reside on the perimeter of the open channel 20c holding the ET tube 50 and is not required to receive the ET tube 50. Rather, the short tube 20t can be spaced apart from the ET tube open channel 20c of the mouthpiece 20' (i.e., and/or not defining an entry into the ET channel 20c and not holding the ET tube 50). It is noted that the term "interlock" and derivatives thereof means that the two components are physically attached to one another in a stable manner that can resist separation during normal intended use at least while compressive pressure/force is applied by a user, but does not require an actual locking relationship. The handle 40' and mouthpiece 20' can cooperate to provide an intuitive and easy-to-use arrangement to facilitate use without requiring laborious training.

As shown in FIGS. 15A-15H, the handle 40' can have an interlocking segment 140 that resides in the short tube 20t to form a male/female interlocking attachment. The short tube 20t can include a cavity 120 for receiving the interlocking handle segment 140. The interlocking segment 140 can comprise a downwardly extending primary member 140p that extends a distance below a primary bottom surface 40b of the handle 40' and is snugly received into an interior cavity 120 (i.e., receptacle) of the short tube 20t.

The handle 40, 40' can be configured to have a mechanical and/or visual guide for placing the handle 40, 40' into the proper orientation into the mouthpiece 20, 20'. The attachment can be intuitive and easy-to use, even for first time users.

The short tube 20t can include guides/grooves and/or visual indicia of orientation and attachment features for facilitating proper interlocking and/or attachment to the handle 40'.

Figure 15A:
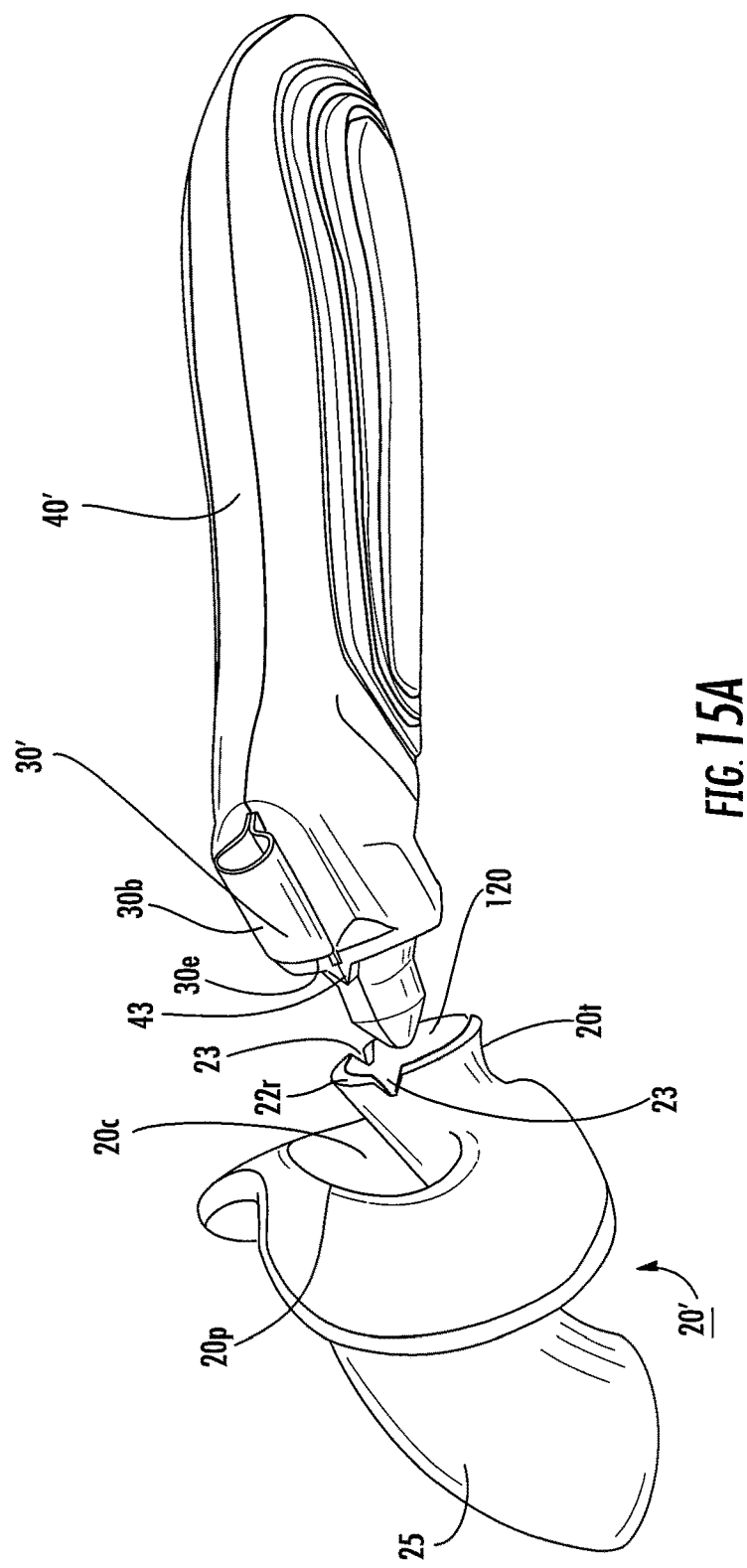
FIG. 15A is a top, side perspective view of the cutting member in cooperating alignment for attachment to a short tube of the mouthpiece according to embodiments of the present invention.

The short tube 20t that engages the handle interlock segment 140 can have a closed cavity or an open cavity. The cavity 120 (and wall thereof) can taper inward from a larger outer size at the rim 22r to a smaller innermost size. The cavity 120 can be closed as shown, or open or partially open. The cavity 120 can have a shape that corresponds to/matably receives the primary interlock member 140p. The primary interlock member 140p can have a length that is between about 0.25 inches and 4 inches, typically between about 0.25 inches and about 1 inch, such as about 0.25 inches, about 0.3 inches, about 0.4 inches, about 0.5 inches, about 0.6 inches, about 0.7 inches, about 0.8 inches 0.9 inches and about 1 inch. The cavity 120 can have a depth that corresponds to the length of the primary interlock (projecting) member 140p, as shown in FIG. 15G, or may be slightly larger. The cavity 120 can have a depth between about 0.25 inches and 4 inches, typically between about 0.25 inches and about 1 inch, such as about 0.25 inches, about 0.3 inches, about 0.4 inches, about 0.5 inches, about 0.6 inches, about 0.7 inches, about 0.8 inches 0.9 inches and about 1 inch As shown in FIGS. 16C-16F, the first and second handle members 41, 42 can each hold half 140a, 140b of the primary interlock member 140p so that adjacent flat surfaces 140f can abut when in the cavity 120 of the short tube 20t and/or when the first and second handle members 41, 42 are held together. FIG. 15F illustrates the center split line 140s between the attached handle members 41, 42.

The primary interlock member 140 can have a hollow interior (FIG. 16F) or may be solid or partially hollow.

Figure 16A:
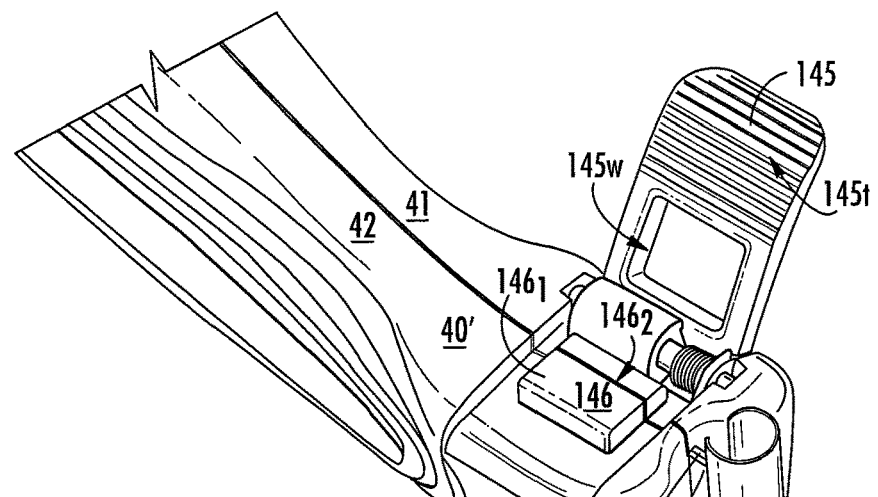
FIG. 16A is a top perspective view of another embodiment of a device for endotracheal tube changeout with a pivoting clasp according to embodiments of the present invention.
Figure 16B:
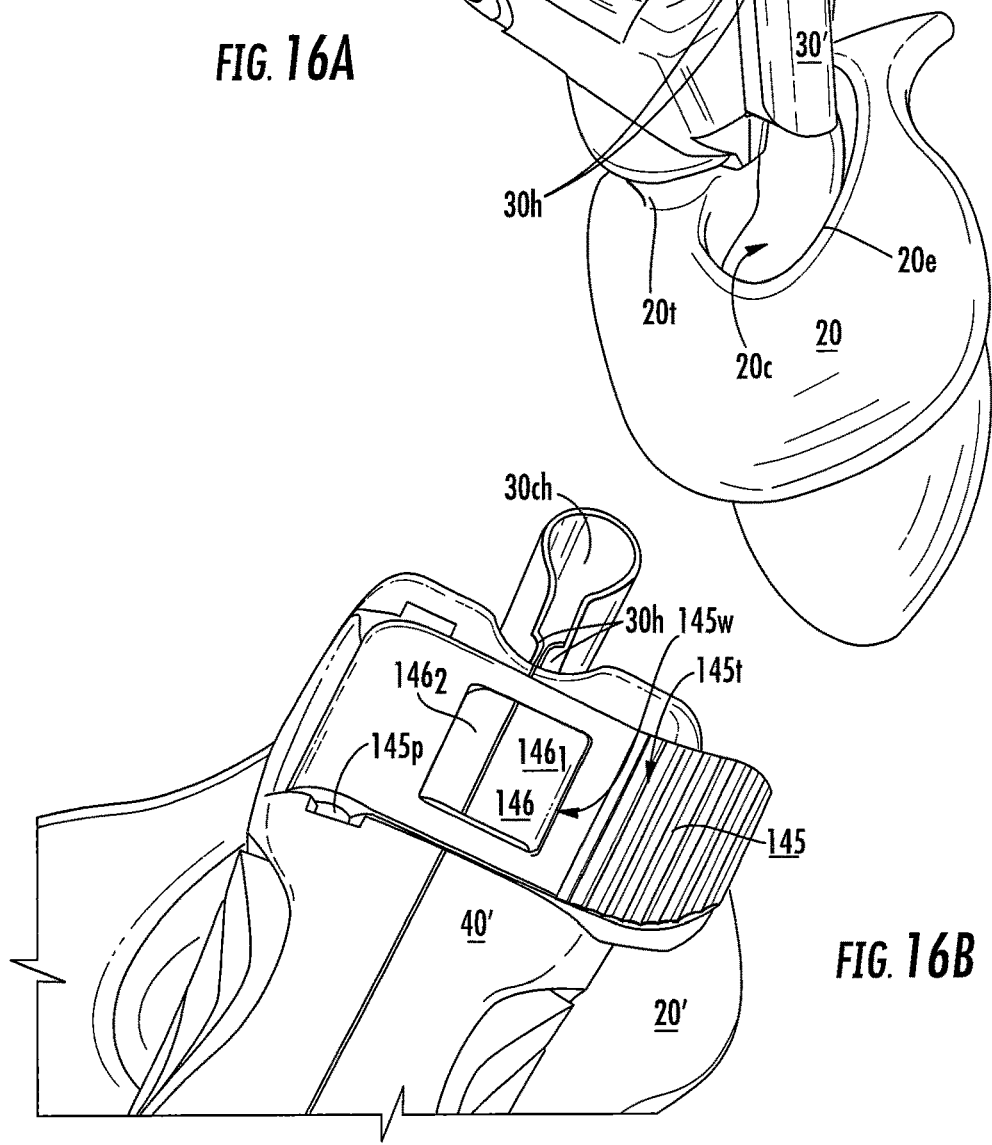
FIG. 16B is an enlarged top perspective view of the device shown in FIG. 16A with the clasp in the lock orientation according to embodiments of the present invention.
Figure 16C:
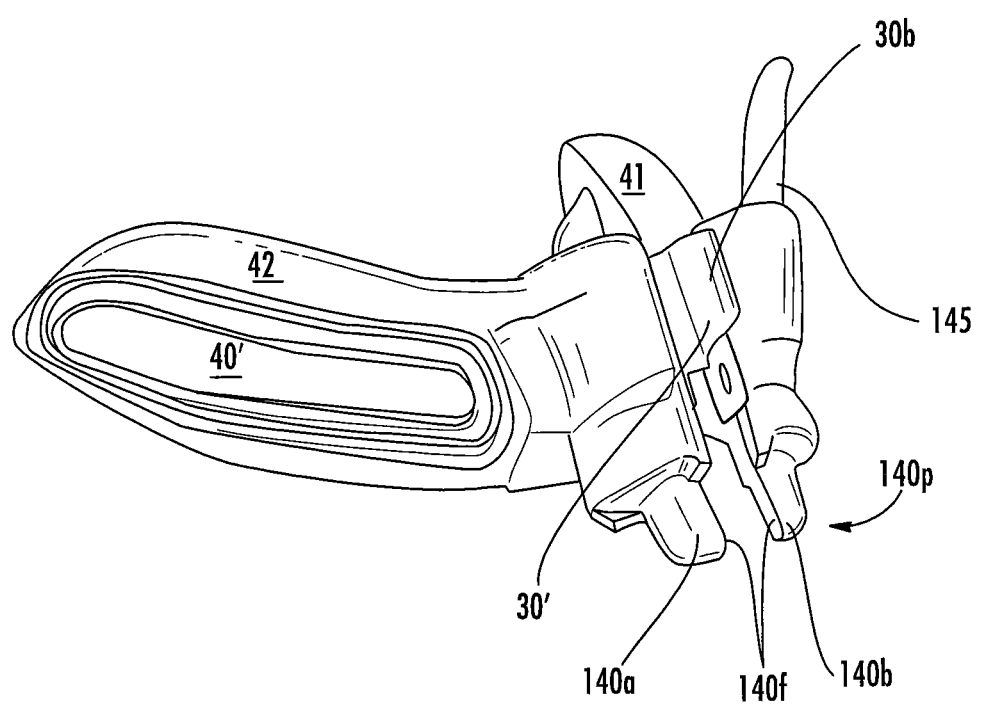
FIG. 16C is a front, side perspective view of the device shown in FIG. 16A, shown in an open or partially open (delatched) configuration according to embodiments of the present invention.
Figure 16E:
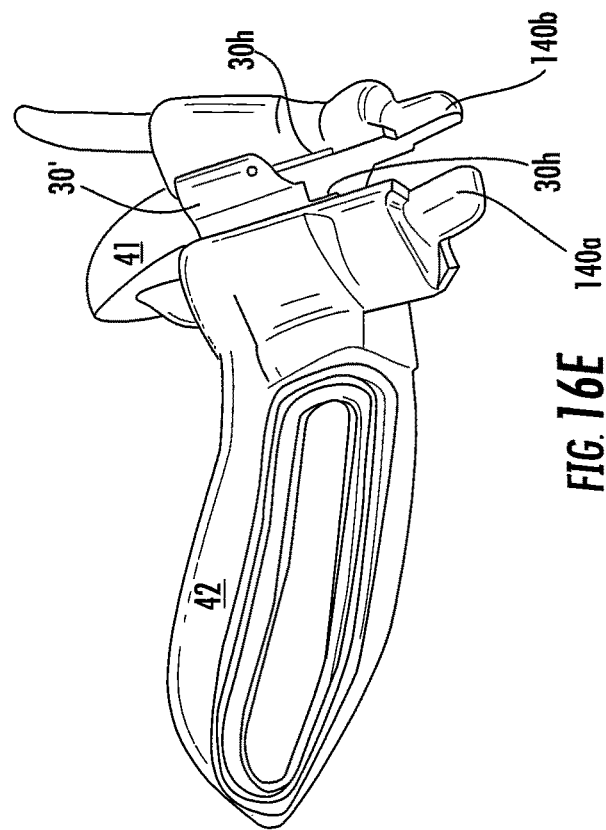
FIGS. 16D and 16E are front, side perspective views of exemplary open (delatched) configurations of the handle with the cutting/slicing blade according to embodiments of the present invention.
Figure 16D:
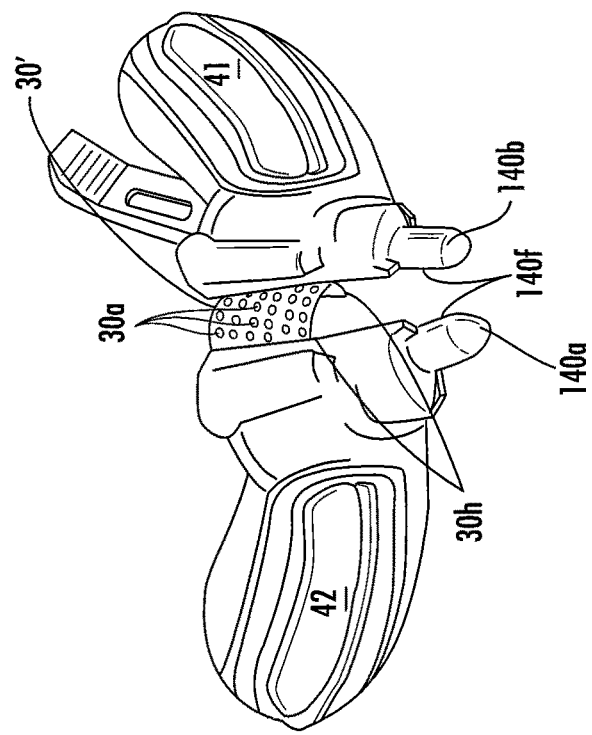
Figure 16F:
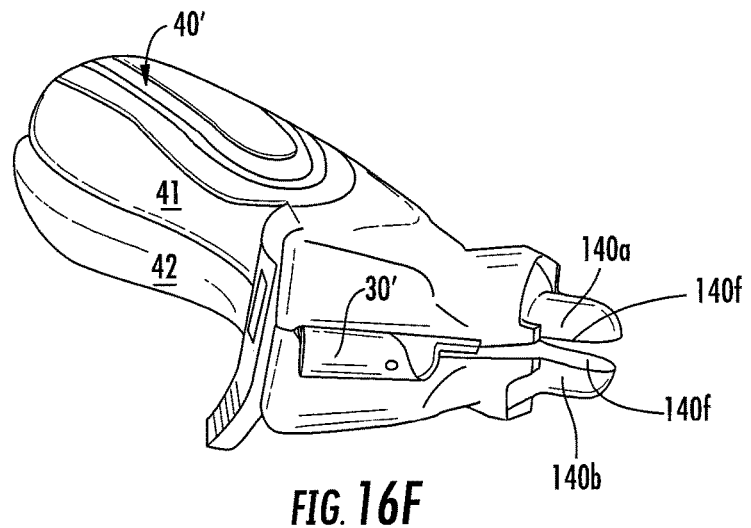
FIG. 16F is a front perspective view of the exemplary latched configuration of the handle shown in FIG. 16E with the cutting/slicing blade according to embodiments of the present invention.

In some embodiments, as shown in FIG. 16F, when the handle members 41, 42 are latched together with latch 145 but prior to attachment to the cavity/receptacle 120 of the interlock channel of the short tube 20t, the pair of primary interlock members 140a, 140b can be spaced apart but proximate to each other (typically with respective flat surfaces facing each other). Entry into the receptacle 120 can force the members 140a, 140b to abut each other and interlock with the mouthpiece 20'.

However, where a projecting interlock member 140 is used, it may be entirely held on one handle member rather than partially on one and partially on the other where two cooperating handle members are used to form the handle.

Figure 15B:
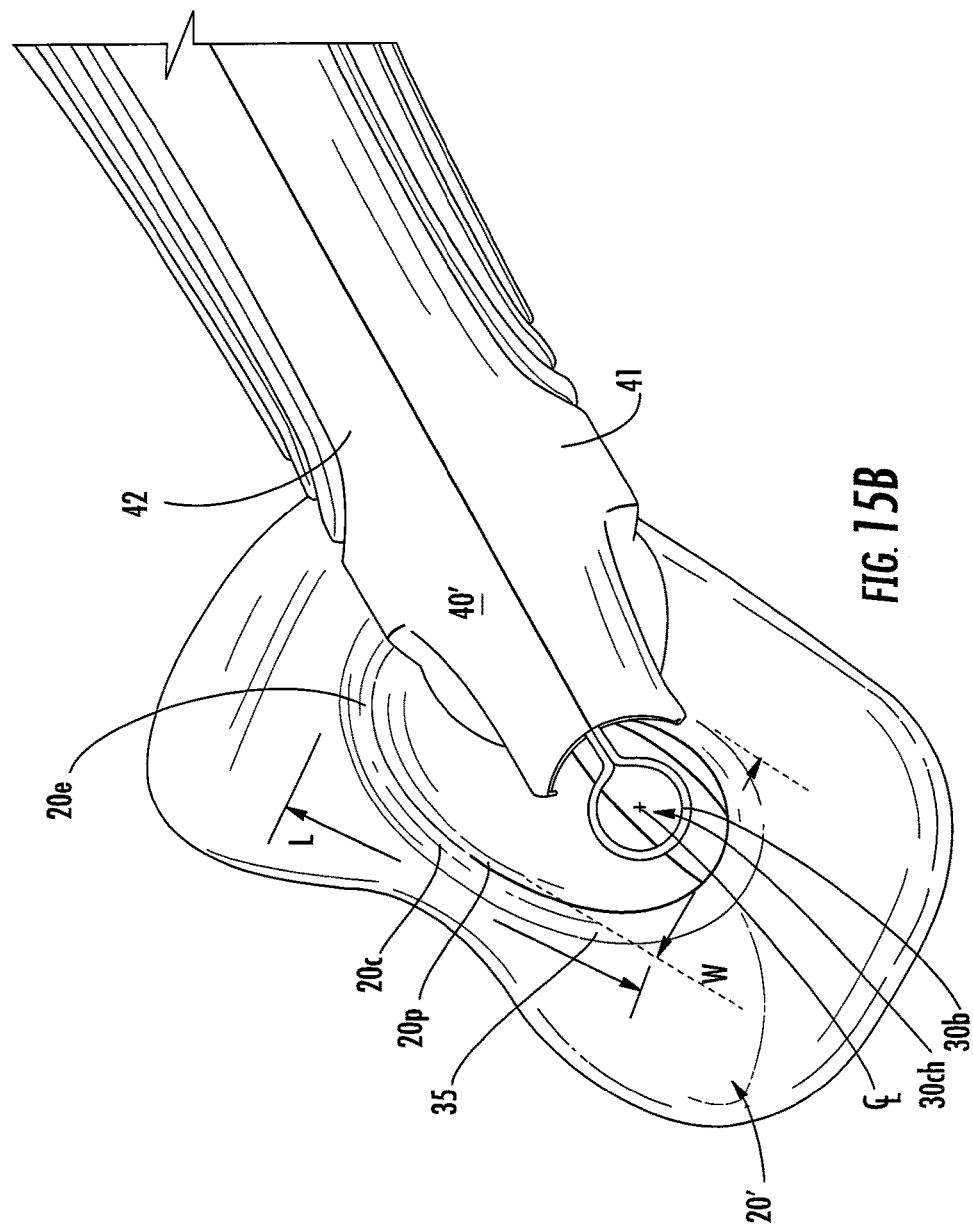
FIG. 15B is an enlarged top perspective view of the device shown in FIG. 15A.
Figure 15C:
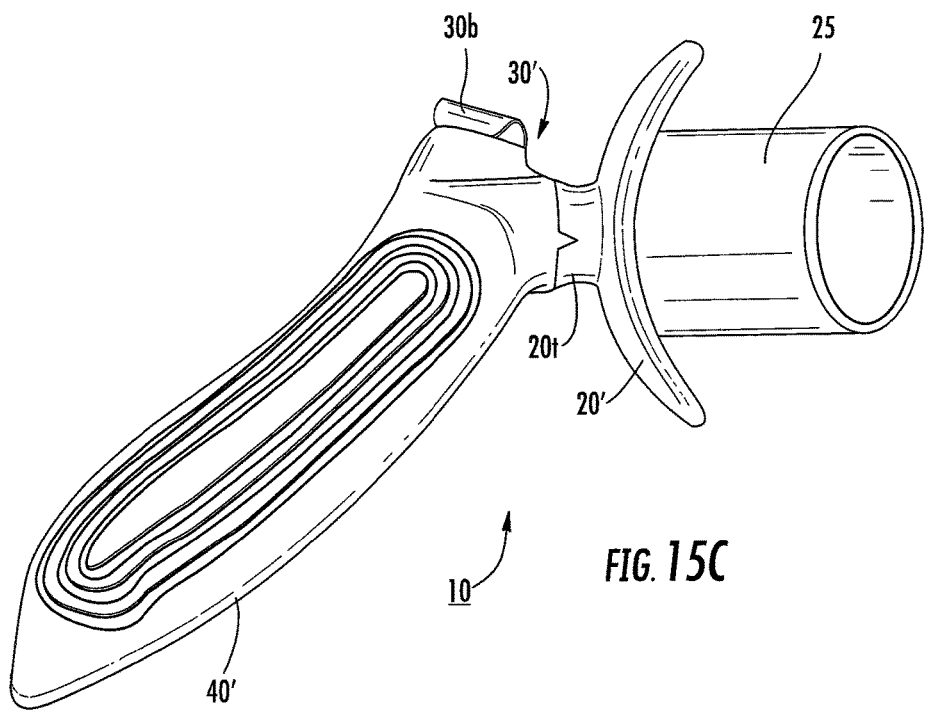
FIG. 15C is a caudal, inferior, bottom perspective view of the device shown in FIG. 15A.
Figure 15D:
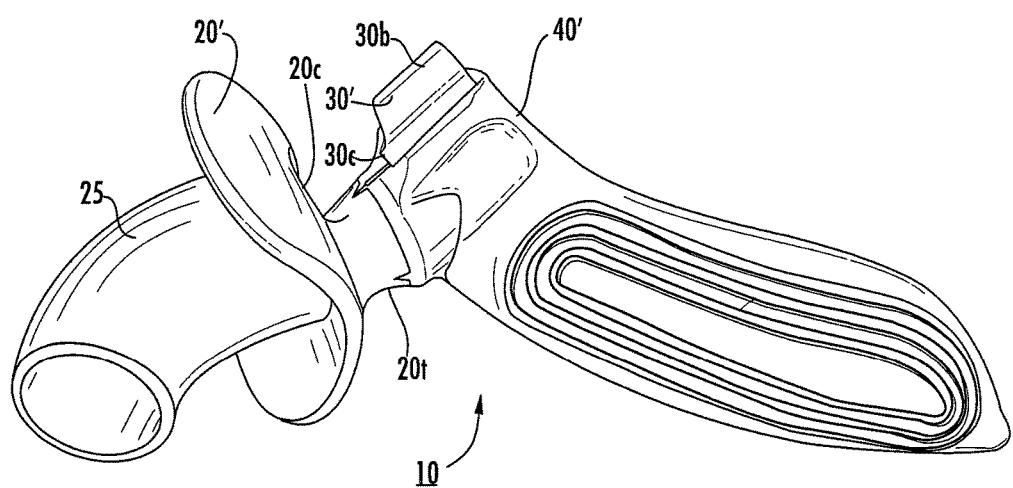
FIG. 15D is an enlarged caudal, bottom, side perspective view of the device shown in FIG. 15A.
Figure 15E:
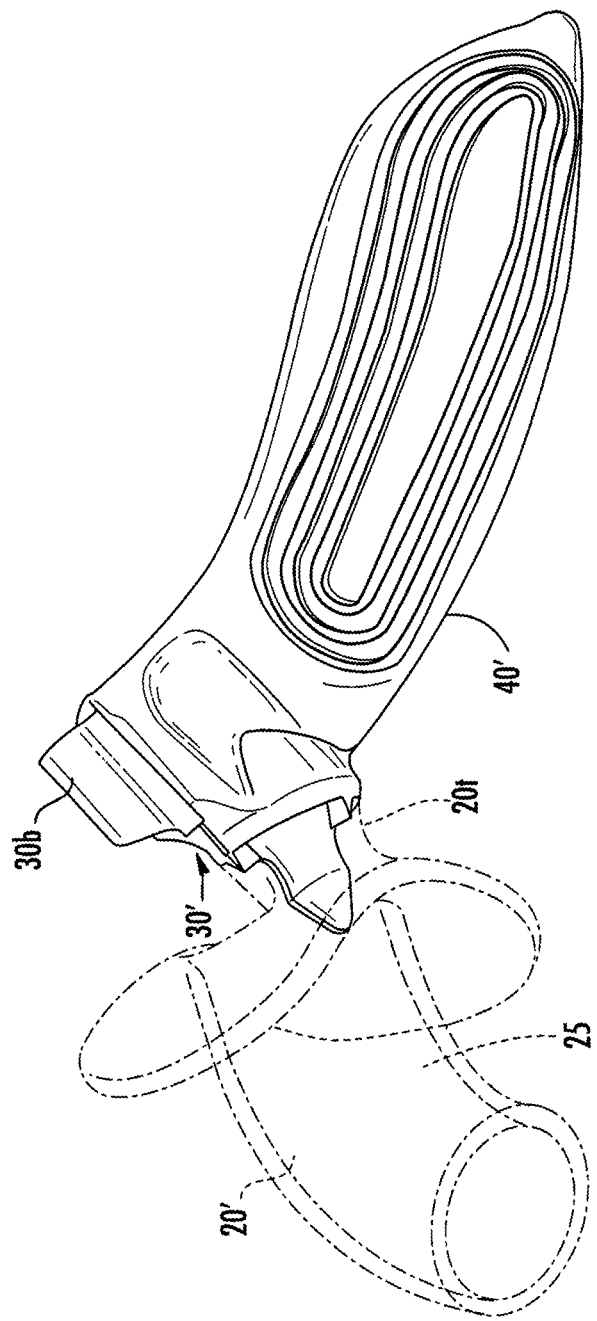
FIG. 15E is a side perspective view of the device shown in FIG. 15A but illustrating the mouthpiece in a visually transmissive configuration to illustrate an exemplary nesting of the mouthpiece engagement end of the handle according to some embodiments of the present invention.
Figure 15G:
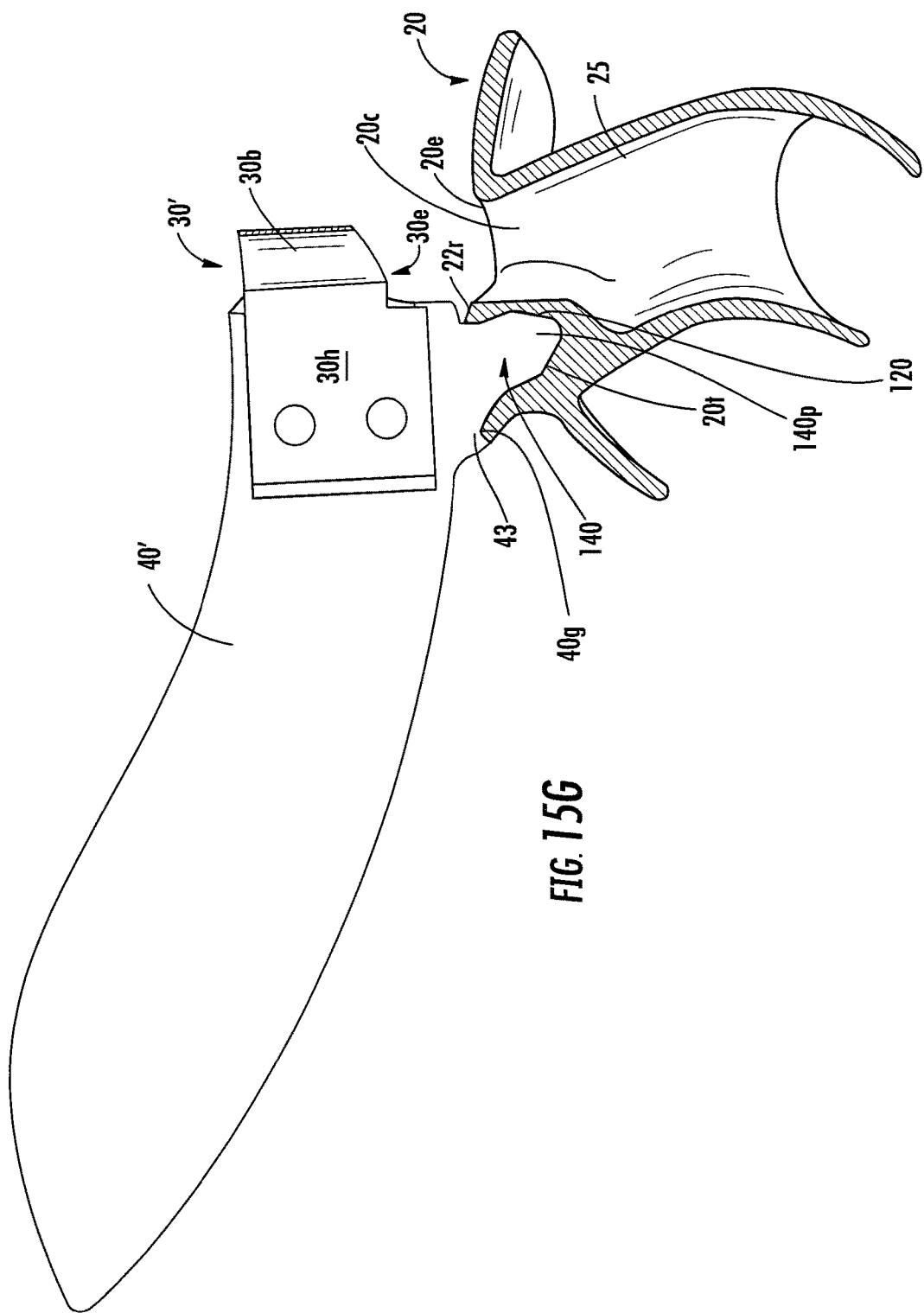
FIG. 15G is a hemi-section view of the handle and mouthpiece of the device shown in FIG. 15A.
Figure 15H:
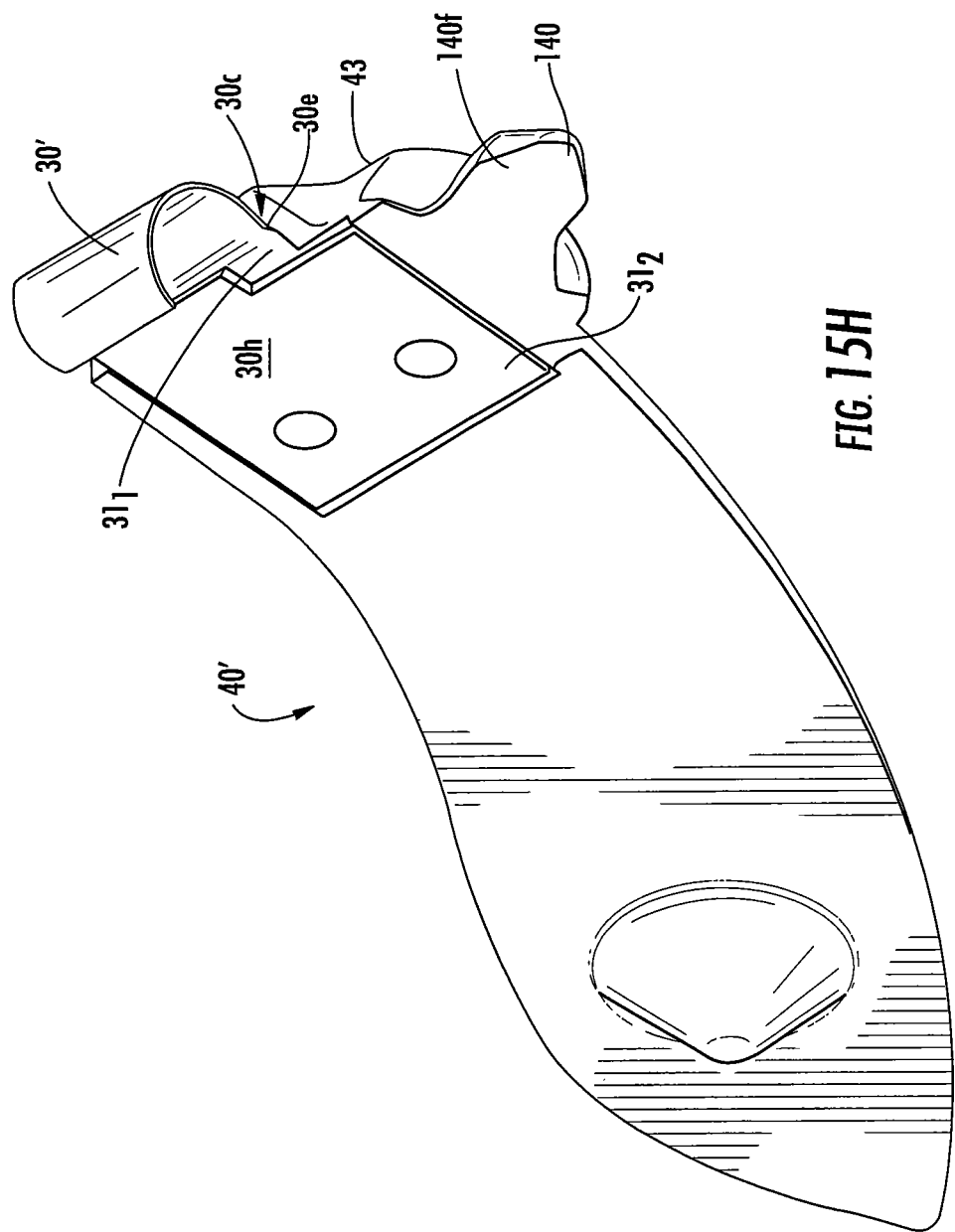
FIG. 15H is a bottom, side perspective view of one handle member of the handle shown in FIGS. 15A and 15F according to some embodiments of the present invention.

FIG. 15B illustrates that the end of the handle holding the cutting blade 30' can be arcuate.

The interlocking segment 140 can include a groove 40g that surrounds the primary member 140p. As shown in FIG. 15G, for example, in position, the groove 40g can rest against the rim 22r of the short tube 20t. However, other interlocking configurations of the mouthpiece 20, 20' and handle 40, 40' can be used. For example, the handle 40 can include a recess and the mouthpiece can have a protrusion, e.g., the short tube 20t can be solid and form the protrusion, and the handle 40' can have a recess that interlocks with the short tube 20t of the mouthpiece. In other examples, "press and rotate" or "press and twist", and/or screw/threaded configurations may be used for interlocking the handle 40' and mouthpiece 20'.

Figure 17A:
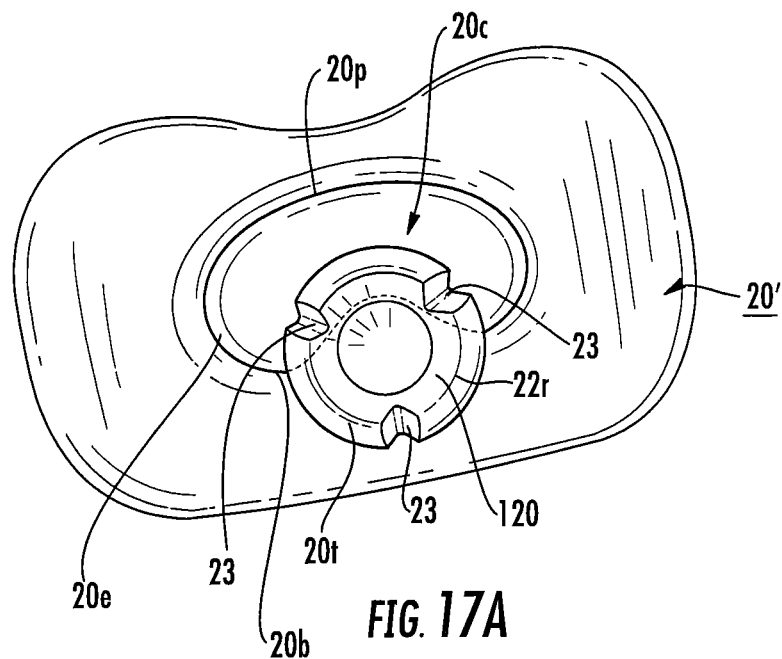
FIG. 17A is an enlarged top perspective view of a mouthpiece according to some embodiments of the present invention.
Figure 17B:
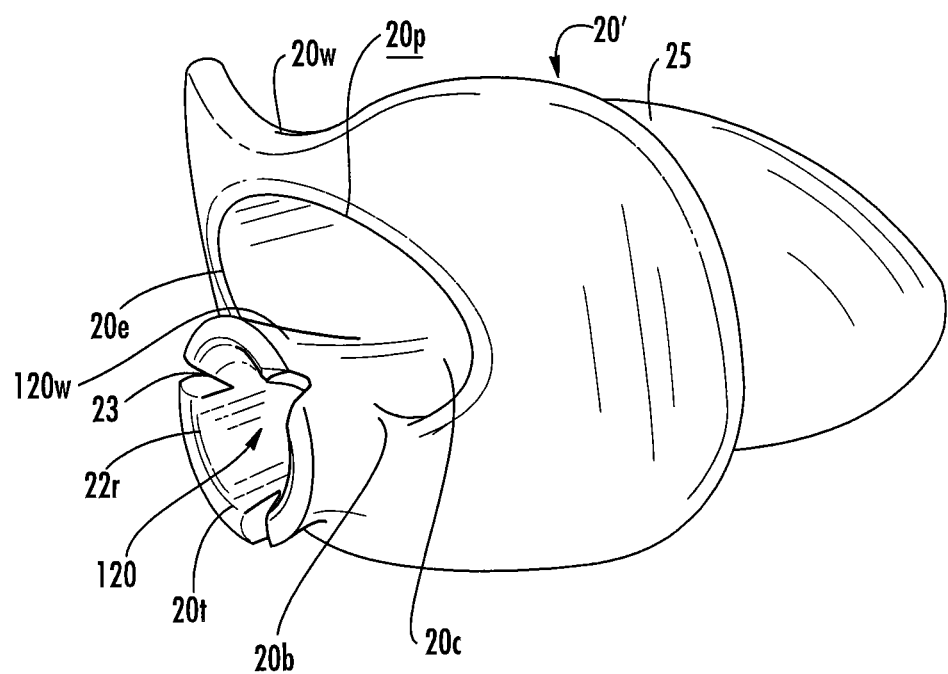
FIG. 17B is a greatly enlarged side perspective view of the mouthpiece shown in FIG. 17A according to embodiments of the present invention.
Figure 17C:
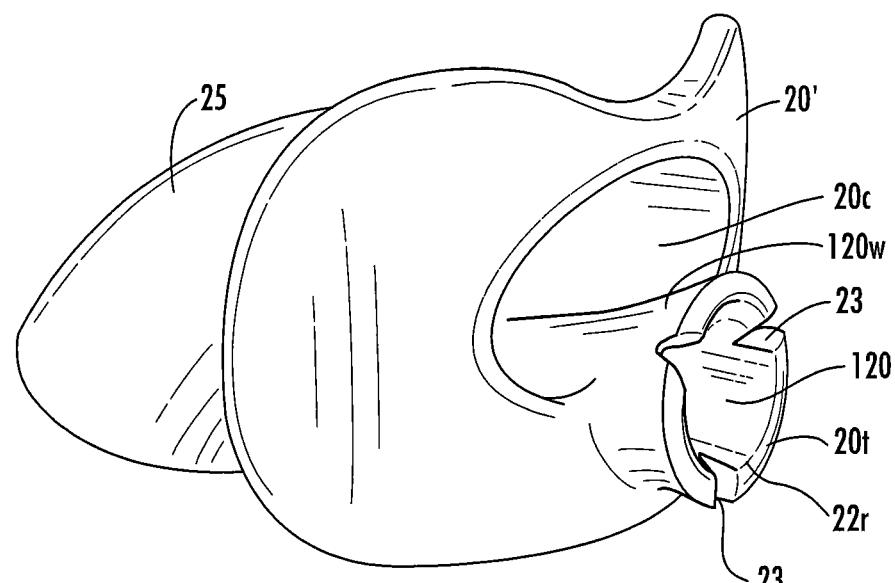
FIG. 17C is a greatly enlarged opposing side perspective view of the mouthpiece shown in FIG. 17B.
Figure 17D:
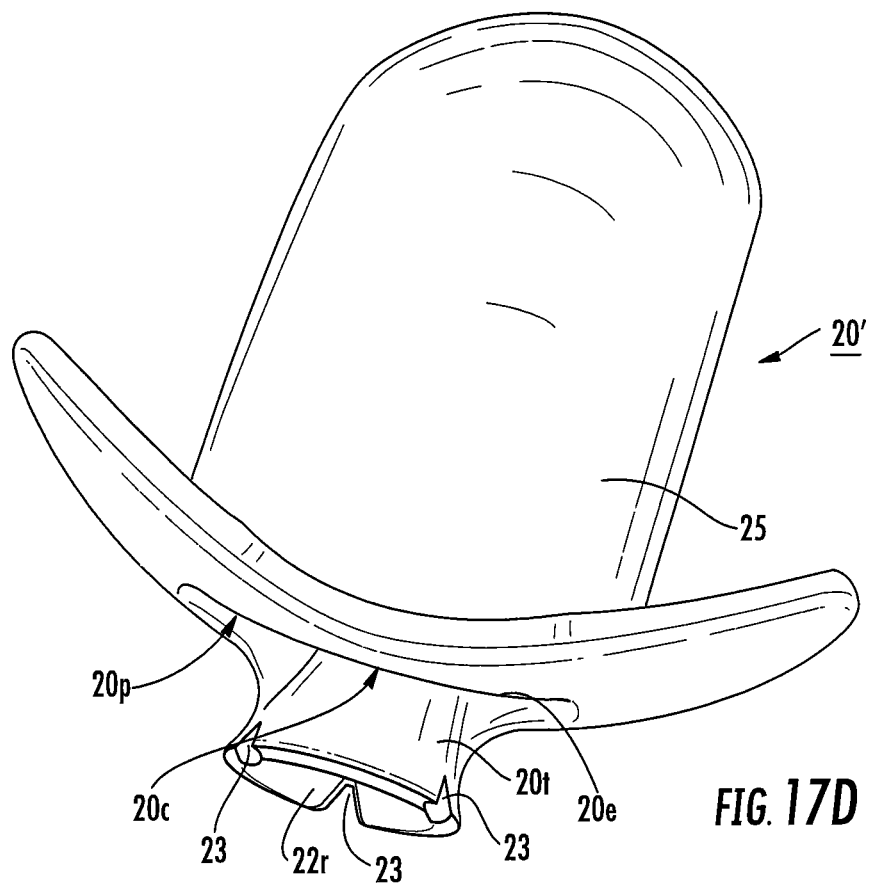
FIG. 17D is a top, cephalad view of the device shown in FIG. 17A.

Referring to FIGS. 15A, 15F and 17A, for example, in some embodiments, the handle interlocking segment 140 can include a plurality of circumferentially spaced apart teeth 43 that can be received into respective notches 23 in the rim 22 of the short tube 20t. Although shown as three teeth 43, one, two or more than three teeth can be used. In other embodiments no teeth are used. The teeth 43 are shown as having "V" shapes that engage "V" shaped notches 23, but other teeth and notch shapes may be used.

Referring to FIG. 15B, the short tube 20t can cooperate with the interlocked handle 40' to position the cutting blade 30 over the open channel 20c of the mouthpiece 20'.

With the handle interlocking segment 140 in the short tube 20t, the centerline C/L of the cylindrical channel 30ch can reside above and within the perimeter 20p of the external aperture 20e of the mouthpiece channel 20c. The handle 40' may be interlocked in either a left-hand or a right-hand orientation on the mouthpiece 20'. As shown in FIG. 15B, the handle 40' is held by a user's left hand (by way of example).

As shown, for example, in FIG. 15F, the band 30b can comprise a suitably sharp cutting surface 30e. The band 30b can be metallic, typically surgical grade stainless steel, and may directly and snugly encase/contact the endoscope (bronchoscope) during use. The band 30b can have internal surfaces that have increased friction such as foam, rubber or embossed surfaces or fenestrations 30a (FIG. 16D) to firmly abut/secure the endoscope during a procedure.

Referring to FIGS. 15B, 15G, 16A, and 17A-17D, for example, the open (ET tube) channel 20c can have an elongate external port/opening/aperture 20e that merges into the internal channel 20c containing the ET tube 50. As shown in FIG. 15B, the port/opening/aperture 20e can have a maximal width dimension "W" that is less than its maximal length dimension "L" and can merge into the channel of the bite block 25. The external opening/aperture 20e can be substantially oval or elliptical and allow the handle 40, 40' to be used from a right or left side of a patient. The port 20e of the mouthpiece 20' can be a single, oval-shaped port that allows the "old" tube 50 to come out the right or left side. That is, the "old" ET tube 50 can be pulled to the left or right side of the mouthpiece 20' for removal and splitting based on sliding contact, upward against the cutting blade 30'.

The handle 40' can be interlocked to the mouthpiece 20' so that the cutting blade 30' faces the right or left side of the mouthpiece (or even the top or bottom side of the mouthpiece 20', although not typical). The external channel port/aperture 20e can have a 35 mm×20 mm (L×W) dimension, in some embodiments.

The handle 40' can be inserted into the short tube 20t to be able to extend in different lateral, medial and/or cephalad directions, depending on physician preference and/or patient access.

The at least one short tube 20t can reside above but longitudinally outside the perimeter 20p of the external port 20e. The handle interlocking segment 140 can releasably interlock to a respective short tube 20t so that the cutting blade 30' extends inward from the short tube 20t to be positioned above but inside the perimeter 20p of the external port 20e.

Still referring to FIGS. 17A-17D, the external aperture/opening 20e of the mouthpiece 20' can have a perimeter shape 20p that is curvilinear and elongate in the length dimension "L". The short tube 20t can reside medially, adjacent a bottom, caudal side 20b of the perimeter 20p. The external top, cephalad-wall 20w of the mouthpiece can be curved to comfortably fit under the nose of a patient. The short tube 20t can be configured with an upwardly extending wall 120w (in the orientation shown in FIG. 17B) that tapers to be larger at the top.

In some embodiments, the mouthpiece 20' can be a monolithic molded member and the inner wall 120w of the short tube 20t can be a bounding surface (wall) of a segment of the perimeter 20p, shown at a bottom perimeter, of the external port/opening/aperture 20e of the mouthpiece. In other embodiments, the short tube 20t can be positioned at other locations on the mouthpiece 20'. However, the short tube 20t can be formed as a separate component that can be attached to the mouthpiece 20'. Further, while one short tube 20t is shown in FIGS. 17A-17D, two or more short tubes 20t may be used. Also, the location of the short tube 20t, whether single or a plurality, can be laterally offset from a center of the primary mouthpiece channel 20c.

FIGS. 16A and 16B illustrate that the handle 40' can include a pivotable latch or clasp 145 that is pivotably attached 145p to one of the cooperating first and second handle members 41, 42 to lock against a surface feature or latch member 146, such as a raised pad. The latch 145 can have a window 145w that closes against a surface feature or member on the adjacent handle member without the latch. The raised pad 146 can be configured as a pair of adjacent pads $146_1$, $146_2$, one on upper surface of each of the first and second handle members 41, 42. Once the old tube is removed, the clasp 146 can be released and the first and second handle members 41, 42 can be automatically pushed (spring) apart. While shown on the first handle member 41 to close when pushed to the left as shown in FIG. 16A, the latch can be configured to be pivotably attached to the right side member 42 and close by pivoting to the right over the other member 41.

As shown in FIG. 16C, for example, the cutting blade 30' can comprise a spring-steel cutting blade that "springs" laterally outward to open or partially open when the clasp 146 or other locking member is opened/unlocked/released. The clasp 145 can include a textured grip surface 145t. Thus, the handle members 41, 42 can be configured to spring apart once the clasp 146 is open for faster separation during a procedure to allow the new tube to be swiftly inserted over the bronchoscope with the cutting blade 30 out of the way.

At least one split location pin and/or other attachment member(s) can be used to align/join the first and second handle members 41, 42 for stability.

Figure 16G:
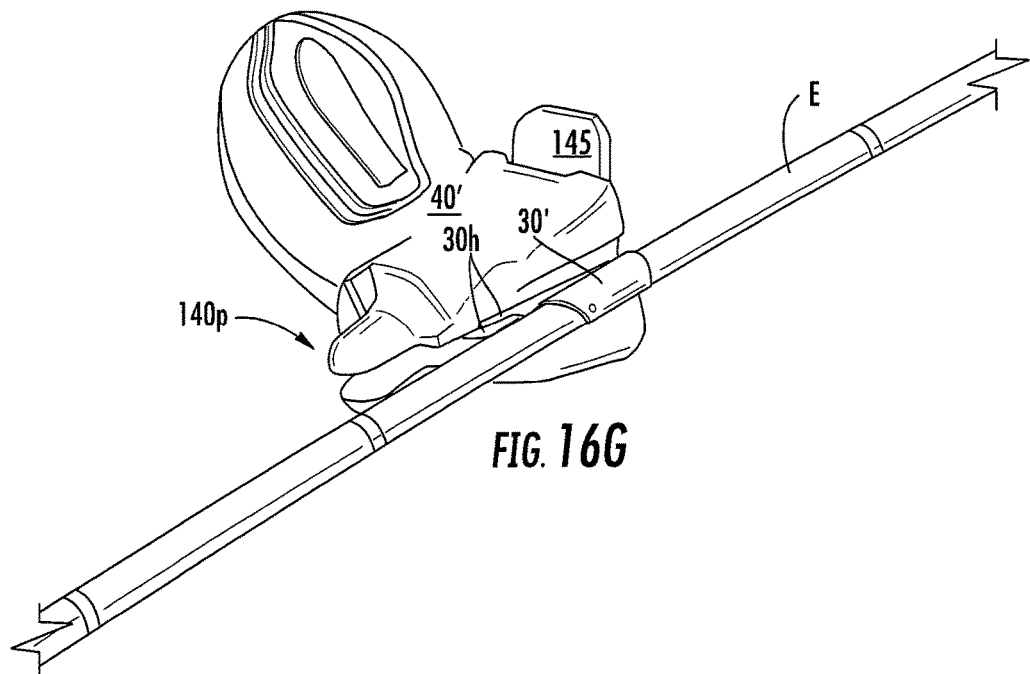
FIG. 16G illustrates the handle shown in FIG. 16E with the blade closed against the fiberoptic (endo/broncho)scope according to embodiments of the present invention.

FIGS. 16C, 16D and 16E illustrate exemplary handles 40' in an open or partially open/unlatched configuration. As shown, the handle members 41, 42 can be rotated apart as can the pair of interlock members 140a, 140b. The planar segments 30h of the metal cutting blade attached to the handle members 41, 42 can also separate from each other. Compare, for example, the adjacent, parallel (optionally abutting) configuration in FIGS. 16A, 16B and 16G with the spaced apart configuration shown in FIGS. 16D and 16E. The blade 30' can be pre-shaped/pre-formed to have a curved configuration when open/partially open.

FIG. 16D illustrates the metal band forming the cutting blade 30' with a fenestrated configuration, e.g., at least one aperture through the wall of the blade 30'. The aperture(s) 30a can include a respective smooth perimeter segment(s) to allow a skin of the scope E to press into or through the aperture(s) 30a without damaging the outer scope membrane or material to provide (additional) friction/grip features for the cutting member 30' to engage the shaft of the endoscope/bronchoscope E. The apertures 30a can be regularly or irregularly spaced apart and may include 1-100 or more apertures of the same or different sizes and shapes.

The handle 40, 40' can have various form factors and shapes. The handle 40, 40' can have a lightweight but sufficiently rigid material to be able to provide the appropriate force to hold the endoscope E in position while the old tube 50 is pulled against the cutting blade 30, 30'. The handle 40, 40' can comprise an ergonomic spring-foam and/or elastomeric or polymeric material. In some particular embodiments, the handle 40, 40' can have maximal dimensions of 150 mm (lateral length)×35 mm (width)×50 mm (longitudinal length).

It is noted that some unexpected variation in endoscope (bronchoscope) diameter has been discovered. For example, two 5.7 diameter scopes have been found to have a 5.3 mm diameter. In some embodiments, the band 30b can have a 5.4 mm blade opening 30ch for 5.3 mm scope diameters. In use, actual measurements with a micrometer or a suitable metrology lab or OEM quality assurance certification of actual measurement for a respective scope may be appropriate for selecting blade sizes 30' for suitable channel diameters 30ch. It is also contemplated that the band 30b can be adjustable in diameter or to include surface features that can accommodate various different size scopes.

The band 30b can be sized and configured to provide a firm grip on the scope without crushing delicate fiber optics. The band 30b can be the grip member 35 described above or be used with another member as a cooperating grip member.

The band 30b can be configured to maintain a desired orientation/position of the cutting edge 30e by keeping the opposing flat portions 30h together during the cutting process. The band 30b can, in some embodiments, have a precision circumference to match a respective endoscope within about 0.5 mm, 1 mm or 2 mm. The band 30b can define a circle of a suitable (corresponding) diameter when the two opposed flat (straight) segments 30h take on a flat mating as shown in FIG. 15F and also allows the band 30b to open and the ends move apart without breaking.

Figure 18:
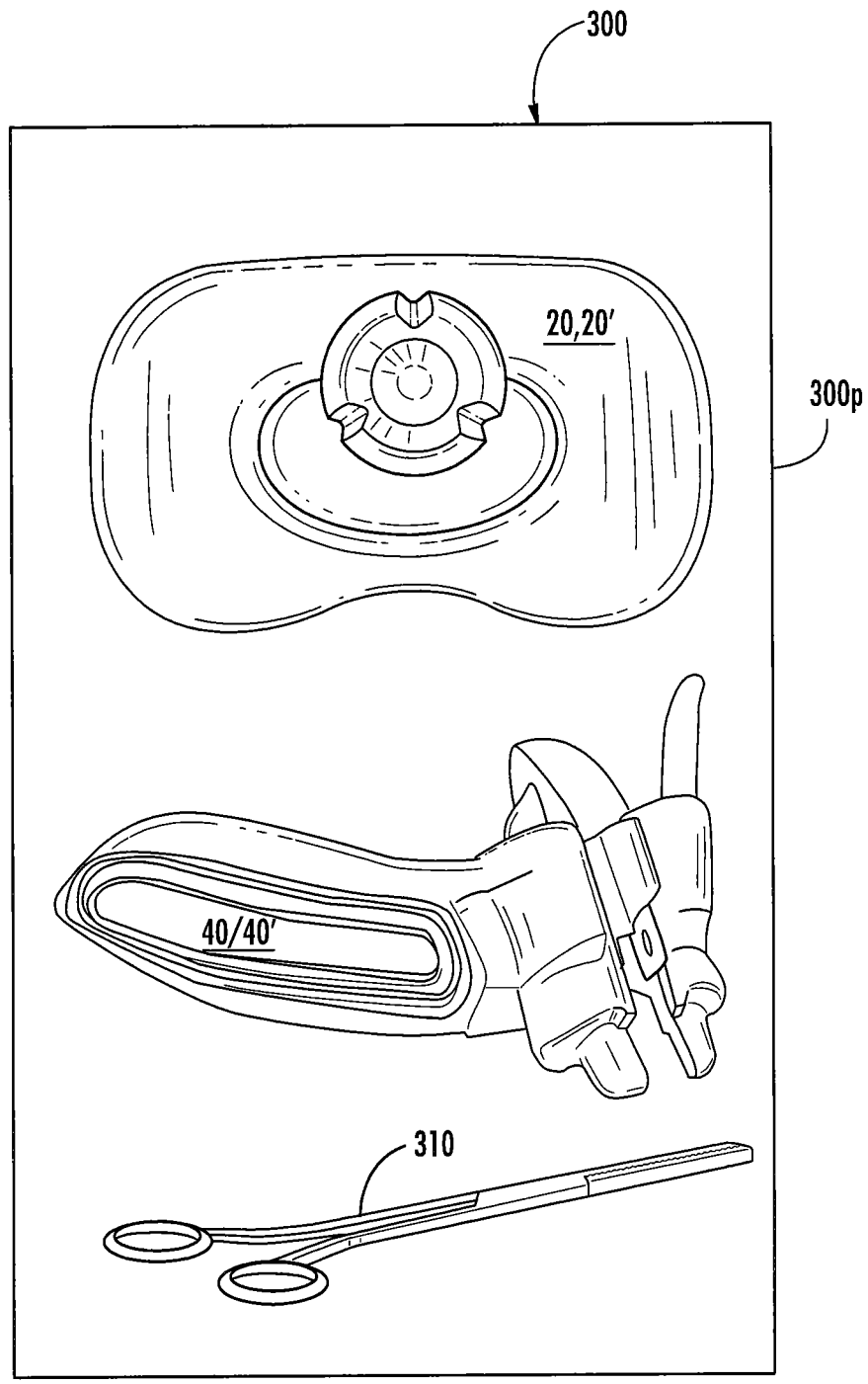
FIG. 18 is an exemplary set of medical devices that can be provided in a ready-to-use kit to facilitate a rapid endotracheal tube changeout according to embodiments of the present invention.

Referring now to FIG. 18, a set of surgical tools can be provided as a kit 300 in a sterile package 300p. The kit 300 include a clamp 310, such as a Kocher clamp, hemostat or forceps or toothed clamp, and the handle 40, 40' with the cutting blade 30, 30'. The term "Kocher clamp" refers to a rigid, straight hemostat with interlocking teeth on the tip. The kit may optionally include a surgical knife blade (e.g., a #11 surgical knife blade) as a back-up or supplemental cutting device.

Optionally, the mouthpiece 20, 20' may also be included in the kit 300.

The kit 300 can be provided with the cutting blade 30, 30' pre-attached to the handle 40, 40' and ready to use. Alternatively, different size blades 30' with a pre-formed curved segment of a defined radius and/or diameter may be included in a single kit for user selection in situ.

It is noted that the handle 40, 40' may be suitable for use for other procedures and is not limited to the embodiments discussed specifically herein. Similarly, the mouthpiece 20, 20' may be suitable for facilitating other procedures and is not limited to the ET tube changeout described hereinabove. For example, the handle 40' and mouthpiece 20' can be used to stabilize an endoscope during a bronchoscopic biopsy within the trachea or bronchus.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

That which is claimed:

1. A tracheal tube device, comprising:
a mouthpiece comprising an external port merging into an open internal channel sized and configured to allow an endotracheal tube to extend therethrough into a trachea of a subject, the external port having a perimeter, wherein the mouthpiece also comprises at least one short tube with a cavity residing above the external port; and
a handle holding a cutting member and comprising at least one interlock member that interlocks to the mouthpiece,
wherein the mouthpiece has a monolithic molded body with a rim that allows the handle interlock member to interlock to the mouthpiece to be able to selectively extend in either a right or left laterally extending direction.

2. The device of claim 1, wherein, in an operative configuration, the handle extends laterally away from the mouthpiece to position a distal end thereof at between 3-10 inches away from the mouthpiece, wherein the handle interlock member interlocks to the at least one short tube and the cutting member comprises a cutting blade that resides inward of a respective short tube to be positioned above but inside the perimeter of the external port.

3. The device of claim 1, wherein, in use, the handle is capable of being held by the mouthpiece to be able to selectively and laterally extend to either a right or left side of a patient, and/or in a caudal orientation to the patient.

4. The device of claim 1, wherein the handle comprises:
first and second cooperating handle members that are capable of opening and closing relative to each other and that hold a metallic member defining a cutting blade therebetween, and
a pivotable latch member residing on one of the first and second handle members configured to latch and unlatch the first and second members.

5. The device of claim 4, wherein the first and second handle members comprise an outer upper surface, each with aligned raised pads, and wherein the latch comprises a window that encases the aligned raised pads in a latched configuration.

6. The device of claim 1, wherein the short tube has an outer rim, wherein the at least one handle interlock member comprises a lower surface with a circumferentially extending groove, and wherein the groove is configured to abut the rim of the short tube.

7. The device of claim 1, wherein the cutting member is configured as a malleable unitary surgical metallic band having two ends that wrap together to define a longitudinally extending channel and a cutting edge.

8. A tracheal tube device, comprising:
a mouthpiece comprising an external port merging into an open internal channel sized and configured to allow an endotracheal tube to extend therethrough into a trachea of a subject, the external port having a perimeter, wherein the mouthpiece also comprises at least one short tube with a cavity residing above the external port; and
a handle holding a cutting member and comprising at least one interlock member that interlocks to the mouthpiece,
wherein the handle comprises first and second cooperating handle members that can open and close relative to each other and that hold a metallic member defining the cutting member therebetween, wherein the metallic member has a longitudinally extending substantially cylindrical segment held by first and second spaced apart planar segments, wherein the first planar segment is attached to the first handle member and the second planar segment is attached to the second handle member, and wherein in an operative configuration, the first and second handle members extend laterally away from the mouthpiece while the at least one interlock member resides in the short tube with the first and second planar segments being adjacent and parallel to each other with the cylindrical segment held over the external port of the mouthpiece.

* * * * *

UNITED STATES PATENT AND TRADEMARK OFFICE
CERTIFICATE OF CORRECTION

PATENT NO. : 10,245,055 B2
APPLICATION NO. : 14/740783
DATED : April 2, 2019
INVENTOR(S) : Michael A. Olympio Page 1 of 1

It is certified that error appears in the above-identified patent and that said Letters Patent is hereby corrected as shown below:

On the Title Page

Item (71) Applicant: Please correct "Michael A. Olympio, Winston-Salem," to read -- Michael A. Olympio, MD, Winston-Salem --

Item (73) Assignee: Please correct "Michael A. Olympio, Winston-Salem," to read -- Michael A. Olympio, MD, Winston-Salem --

Signed and Sealed this
Ninth Day of July, 2019

Andrei Iancu
*Director of the United States Patent and Trademark Office*